US009216168B1

(12) United States Patent
Tabuteau

(10) Patent No.: US 9,216,168 B1
(45) Date of Patent: *Dec. 22, 2015

(54) THERAPEUTIC COMPOSITIONS COMPRISING IMIDAZOLE AND IMIDAZOLIUM COMPOUNDS

(71) Applicant: Antecip Bioventures II LLC, New York, NY (US)

(72) Inventor: Herriot Tabuteau, New York, NY (US)

(73) Assignee: ANTECIP BIOVENTURES II LLC, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/540,333

(22) Filed: Nov. 13, 2014

Related U.S. Application Data

(63) Continuation of application No. 14/481,097, filed on Sep. 9, 2014, which is a continuation of application No. 14/288,720, filed on May 28, 2014, now Pat. No. 8,865,757, and a continuation of application No. 14/288,241, filed on May 27, 2014, now Pat. No. 8,901,161.

(51) Int. Cl.
*C07D 233/60* (2006.01)
*A61K 31/4172* (2006.01)
*A61K 31/4164* (2006.01)
*A61K 31/675* (2006.01)

(52) U.S. Cl.
CPC ......... *A61K 31/4172* (2013.01); *A61K 31/4164* (2013.01); *A61K 31/675* (2013.01); *C07D 233/60* (2013.01)

(58) Field of Classification Search
None
See application file for complete search history.

(56) References Cited

U.S. PATENT DOCUMENTS

| | | | |
|---|---|---|---|
| 4,939,130 A | 7/1990 | Jaeggi et al. | |
| 5,869,471 A | 2/1999 | Hovancik et al. | |
| 6,015,801 A | 1/2000 | Daifotis | |
| 6,419,955 B1 | 7/2002 | Gabel et al. | |
| 6,943,155 B2 | 9/2005 | Lichtenberger | |
| 7,658,939 B2 | 2/2010 | Oshlack et al. | |
| 7,704,977 B2 | 4/2010 | Leonard | |
| 8,053,429 B2 | 11/2011 | Cumming et al. | |
| 8,119,159 B2 | 2/2012 | Cumming et al. | |
| 8,323,689 B2 | 12/2012 | Cumming et al. | |
| 8,323,690 B2 | 12/2012 | Cumming et al. | |
| 8,399,023 B2 | 3/2013 | Hanna et al. | |
| 8,772,267 B2 | 7/2014 | Pappagallo | |
| 8,828,431 B2 | 9/2014 | Cumming et al. | |
| 8,859,530 B2 | 10/2014 | Desai | |
| 8,865,757 B1 | 10/2014 | Tabuteau | |
| 8,883,201 B2 | 11/2014 | Leonard | |
| 8,883,203 B2 | 11/2014 | Leonard | |
| 8,901,161 B1 | 12/2014 | Tabuteau | |
| 8,901,162 B1 | 12/2014 | Tabuteau | |
| 8,933,057 B2 | 1/2015 | Hanna et al. | |
| 2002/0033144 A1* | 3/2002 | Thompson | 119/651 |
| 2004/0063670 A1 | 4/2004 | Fox et al. | |
| 2009/0281064 A1 | 11/2009 | Ahmed et al. | |
| 2010/0215743 A1 | 8/2010 | Leonard | |
| 2011/0028435 A1 | 2/2011 | Hanna et al. | |
| 2011/0098252 A1 | 4/2011 | Pappagallo | |
| 2012/0190647 A1 | 7/2012 | Hanna et al. | |
| 2013/0274282 A1 | 10/2013 | Tabuteau | |
| 2013/0303485 A1 | 11/2013 | Tabuteau | |
| 2013/0303486 A1 | 11/2013 | Tabuteau | |
| 2013/0303487 A1 | 11/2013 | Tabuteau | |
| 2013/0303488 A1 | 11/2013 | Tabuteau | |
| 2014/0051669 A1 | 2/2014 | Tabuteau | |
| 2014/0051718 A1 | 2/2014 | Tabuteau | |
| 2014/0249107 A1 | 9/2014 | Tabuteau | |
| 2014/0249108 A1 | 9/2014 | Tabuteau | |
| 2014/0249109 A1 | 9/2014 | Tabuteau | |
| 2014/0249111 A1 | 9/2014 | Tabuteau | |
| 2014/0249112 A1 | 9/2014 | Tabuteau | |
| 2014/0249113 A1 | 9/2014 | Tabuteau | |
| 2014/0249317 A1 | 9/2014 | Tabuteau | |

FOREIGN PATENT DOCUMENTS

| | | |
|---|---|---|
| CN | 101259133 | 3/2008 |
| WO | WO 02087555 | 11/2002 |
| WO | WO 2005063218 | 7/2005 |
| WO | 2005/107751 A1 | 11/2005 |
| WO | WO 2012071517 | 5/2012 |

OTHER PUBLICATIONS

U.S. Appl. No. 14/481,097, filed Sep. 2014, Tabuteau, H.*
Lipton, et al., Cancer Investigation, 20:45 (2002; Suppl. 2).*
Zhang, et al., J. Med. Case Reports, 7:268 (Dec. 13, 2013).*
Clunie, et al., Ann. Rheum. Dis., (Feb. 12, 2014).*
King, et al., Clinical Lung Cancer, 9:179 (2008).*
Dubin, C., Drug Dev. Tech., 10:30 (2010).*
Otrock, et al., Ann. Hematol., 85:605 (Jul. 08, 2006).*
Merrion Pharmaceuticals press release, "Merrion finalises its Phase III development program for Orazol™ in the USA," (Nov. 16, 2010).*
Phase II Study, "Multi-Center Phase II Study to Compare MER-101 20mg Tablets to Intravenous Zometa 4mg in Male Bisphosphonate-Naïve Hormone Refractory Prostate Cancer Patients," NCT00636740 (Feb. 2009).*
Transaction History page of related application U.S. Appl. No. 13/894,244 Oct. 2013.
Transaction History page of related application U.S. Appl. No. 13/894,252 Oct. 2013.
Transaction History page of related application U.S. Appl. No. 13/894,262 Oct. 2013.

(Continued)

*Primary Examiner* — Michael Barker
(74) *Attorney, Agent, or Firm* — K&L Gates LLP; Louis C. Cullman; Brent A. Johnson

(57) ABSTRACT

Therapeutic compositions comprising substituted imidazole or imidazolium compounds may be used for a number of medical purposes, such as treatment of undesirable conditions or diseases, including disease or conditions related to bone, cancer, and/or pain.

21 Claims, No Drawings

(56) References Cited

OTHER PUBLICATIONS

Turner-Stokes, Lynne et al., "Complex regional pain syndrome in adults: concise guidance", Clinical Medicine, 11 (6):596-600 (2011).
US Product Label for Zometa, revised 2012, Prescribing info.
US Product Label for Zometa, revised Sep. 2013, FDA Prescribing Information for Zometa (zoledronic acid) injection.
Van de Beek, Willem-Johan et al., "Susceptibility loci for complex regional pain syndrome", Pain® 103:93-97 (2003).
Van de Vusse, Anton C. et al., "Randomised controlled trial of gabapentin in Complex Regional Pain Syndrome type I [ISRCTN84121379]", BMC Neurology, 4:13: 1-9(2004).
Van der Laan, Lijckle MD, et al., "Severe Complications of Reflex Sympathetic Dystrophy: Infection, Ulcers, Chronic Edema, Dystonia, and Myoclonus", Arch Phys Med Rehabil, 79:424-429 (1998).
Van der Laan, Lycke, MD et al., "Reflex Sympathetic Dystrophy", Hand Clinics, 13(3):373-385 (1997).
Van Offel, J.F. et al., "Influence of cyclic intravenous pamidronate on proinflammatory monocytic cytokine profiles and bone density in rheumatoid arthritis treated with low dose prednisolone and methrotrexate", Clinical and Experimental Rheumatology, 19:13-20 (2001).
Varenna et al., Intravenous clodronate in the treatment of reflex sympathetic dystrophy syndrome. A randomized, double blind, placebo controlled study. J Rheumatol 2000: 27: 1477-1483.
Varenna, Massimo et al., "Treatment of complex regional pain syndrome type I with neridronate: a randomized, double-blind, placebo-controlled study", Rheumatology, 1-9 (2012).
Veldman, Peter HJM et al., "Signs and symptoms of reflex sympathetic dystrophy: prospective study of 829 patients", The Lancet, 342:1012-1016 (1993).
Walker et al., Disease modifying and anti-nociceptive effects of the bisphosphonate, zoledronic acid in a model of bone cancer pain. Pain 100 (2002) 219-229.
Wasner, Gunnar et al., "Traumatic Neuralgias—Complex Regional Pain Syndromes (Reflex Sympathetic Dystrophy and Causalgia): Clinical Characteristics, Pathophysiologic Mechanisms and Therapy", Neurologic Clinics, 16 (4):851-868, (1998).
Wasner, Gunnar et al., "Vascular Abnormalities in Acute Reflex Sympathetic Dystrophy (CRPS I)", Arch Neurol, 56:613-620 (1999).
Weiss et al., Biodistribution and Plasma Protein Binding of Zoledronic Acid, Drug Metabolism and Disposition, vol. 36, No. 10, pp. 2043-2049, 2008.
Yanow, Jennifer et al., "Complex Regional Pain Syndrome (CRPS/RSD) and Neuropathic Pain: Role of Intravenous Bisphosphonates as Analgesics", TheScientificWorld Journal, 8:229-236 (2008).
Zaspel et al., Treatment of early stage CRPS I—cortisone (methylprednisolone) versus bisphosphonate (zoledronic acid). German Congress of Orthopedics and Traumatology. 71st Annual Meeting of the German Society of Trauma Surgery, 93rd Meeting of the German Society for Orthopedics and Orthopedic Surgery, 48th Meeting of the Professional Association of Specialists in Orthopedics. Berlin, Oct. 24-27, 2007. German Medical Science GMS Publishing House; 2007.
Zheng, Jack 2009, Formulation and Analytical development for low dose oral drug products, by John Wiley and Sons, Inc.
Zoledronate Disodium: Treatment of Tumor-Induced Hypercalcemia Angiogenesis Inhibitor, Drugs of the Future 2000, 25(3) 259-268.
Zometa FDA Pharmacology Review, part 1, accessed 2013.
Zometa FDA Pharmacology Review, part 2, accessed 2013.
Zometa FDA Pharmacology Review, part 3, accessed 2013.
Zometa FDA Pharmacology Review, part 4, accessed 2013.
Zometa FDA Pharmacology Review, part 5, accessed 2013.
Zometa Label, Revised: Mar. 2012, Novartis Pharma Stein AG.
Zyluk, A., "The Natural History of Post-Traumatic Reflex Sympathetic Dystrophy", Journal of Hand Surgery (British and European Volume), 23B: 1:20-23 (1998).
Olmsted County, Minnesota. Profile o General Demographic Characteristics: 2000. Source: U.S. Census Bureau, Census 2000—Summary File 1, Matrices P1, P3, P4, P8, P9, P12, P13, P17, P18, P19, P20, P23, P27, P28, P33, PCT5, PCT8, PCT11, PCT15, H1, H3, H4, H5, H11, and H12.
Opinion of the Committee for Orphan Medicinal Products on orphan medicinal product designation, European Medicines Agency, Sep. 2013, pp. 1-3.
Opree et al. "Involvement of the Proinflammatory Cytokines Tumor Necrosis Factor-a, IL-1B, and IL-6 But Not IL-8 in the Development of Heat Hyperalgesia: Effects on Heat Evoked Calcitonin Gene-Related Peptide Release from Rat Skin." The Journal of Neuroscience, Aug. 15, 2000, 20(16):6289-6293.
Orange Book: Active Ingredient Search. FDA/Center for Drug Evaluation and Research, Updated Feb. 28, 2014.
Orazol(R): Novel approach to adjuvant therapy for improving outcomes in breast cancer. Merrion Pharmaceuticals, accessed 2013.
Orcel "Response." Joint Bone Spine 2002; 69; 522-2.
Orcel et al. "Bisphosphonates in bone diseases other than osteoporosis." Joint Bone Spine 2002; 69; 19-27.
Pankaj et al. "Diagnosis of post-traumatic complex regional pain syndrome of the hand: current role of sympathetic skin response and three-phase bone schintigraphy." Journal of Orthopaedic Surgery 2006;14(3)284-90.
Pennanen et al. "Effect of Liposomal and Free Bisphosphonates on the IL-1B, IL-6 and TNFa Secretion from RAW 264 Cells in Vitro." Pharmaceutical Research, vol. 12, No. 6, 1995.
Perez et al. "Evidence based guideline for complex regional pain syndrome type 1." BMC Neurology 2010, 10:20.
Raj "Treatment of Fibrous Dysplasia with Zoledronic Acid Infusion Case Report, Review of Literature and Future Prospectives."WebMD Central, ISSN 2046-1690, Published Nov. 22, 2010.
Raja et al. Complex Regional Pain Syndrome I (Reflex Sympathetic Dystrophy).Anesthesiology 2002; 96:1254-60.
Reclast Label, Revised: Aug. 2011, Novartis Pharma Stein AG.
Reclast Medication Guide. Aug. 2011.
Recommendation on elements required to support the medical plausibility and the assumption of significant benefit for an orphan designation. EMA/COMP/15893/2009. Mar. 2, 2010.
Reid et al. "Comparison of a Single Infusion of Zoledronic Acid with Risedronate for Paget's Disease." N Engl J Med 353:9, Sep. 1, 2005.
Reid et al., Intravenous Zoledronic Acid in Postmenopausal Women with Low Bone Mineral Density. N. Engl. J. Med., vol. 346, No. 9, Feb. 2002.
Rho et al. "Complex Regional Pain Syndrome." May Clin Proc. 2002; 77:174-180.
Ringe "Development of clinical utility of zoledronic acid and patient consideration in the treatment of osteoporosis." Patient Preference and Adherence 2010:4 231-245.
Ringe et al., A review of bone pain relief with ibandronate and other bisphosphonates in disorders of increased bone turnover. Clin. Exp. Rheumatol. 2007; 25: 766-774.
Ripamonti et al. "Decreases in pain at rest and movement-related pain during zoledronic acid treatment in patients with bone metastases due to breast or prostate cancer: a pilot study." Support Care Center (2007) 15:1177-1184.
Robinson et al., Efficacy of pamidronate in complex regional pain syndrome type I. Pain Med 2004; 5:276-280.
Rooij et al. "Familial occurrence of complex regional pain syndrome." Eur J Pain 13 (2009) 171-177.
Rooij et al. "HLA-B62 and HLA-DQ8 are associated with Complex Regional Pain Syndrome with fixed dystonia." Pain 145 (2009) 82-85.
Rousselle et al. "Osteoclastic Acidifaction Pathways During Bone Resorption." Bone vol. 30, No. 4, Apr. 2002: 533-540.
Sandroni, Paola et al., "Complex regional pain syndrome type I: incidence and prevalence in Olmsted county, a population-based study", Pain® 103:199-207, (2003).
Sansoni, Paolo et al., "Inhibition of Antigen-Presenting Cell Function by Alendronate in Vitro", Journal of Bone and Mineral Research, 10(11):1719-1725 (1995).
Schinkel, Christian MD, et al., "Inflammatory Mediators are Altered in the Acute Phase of Posttraumatic Complex Regional Pain Syndrome", Clin J. Pain , 22(3):235-239 (2006).

(56) References Cited

OTHER PUBLICATIONS

Schott GO. Bisphosphonates for pain relief in reflex sympathetic dystrophy? Lancet 1997;350: 1117.
Schwartzman, Robert J. et al., "The Natural History of Complex Regional Pain Syndrome", Clin J Pain, 25 (4):273-280 (2009).
Schwartzman, Robert J., et al., "Outpatient intravenous ketamine for the treatment of complex regional pain syndrome: A double-blind placebo controlled study", Pain® 147:107-115 (2009).
Schwenkreis, P. et al., "Bilateral Motor Cortex Disinhibition in Complex Regional Pain Syndrome (CRPS) Type I of the Hand", American Academy of Neurology, 61:515-519 (2003).
Scientific Discussion. EMEA 2005, pp. 1-24.
Sebastian, Complex regional pain syndrome. Indian J. Past Surg., 44(2): 298-307 (2011).
Seok, Hyun et al., "Treatment of Transient Osteoporosis of the Hip with Intravenous Zoledronate", Ann Rehabil Med, 35:432-435 (2011).
Sevcik, Molly A. et al., "Bone cancer pain: the effects of the bisphosphonate alendronate on pain, skeletal remodeling, tumor growth and tumor necrosis", Pain® 111:169-180 (2004).
Sharma, Amit et al., "A Web-Based Cross-Sectional Epidemiological Survey of Complex Regional Pain Syndrome", Regional Anesthesia and Pain Medicine, 34(2):110-115 (2009).
Sharma, Amit et al., "Advances in treatment of complex regional pain syndrome: recent insights on a perplexing disease", Curr Opin Anaesthesiol, 19:566-572 (2006).
Sigtermans, Marnix J. et al., "Ketamine produces effective and long-term pain relief in patients with Complex Regional Pain Syndrome Type I", Pain® 145:304-311 (2009).
Sommer, Claudia et al., "Recent findings on how proinflammatory cytokines cause pain: peripheral mechanisms in inflammatory and neuropathic hyperalgesia", Neurosience Letters, 361:184-187 (2004).
Sorbera et al., Zoledronate Disodium, Drugs of the Future 2000, 25(3):259-268.
St. Sauver, Jennifer L. et al., "Use of a Medical Records Linkage System to Enumerate a Dydamic Population Over Time: The Rochester Epidemiology Project", Am J. Epidemiol, 173(9):1059-1068 (2011).
Stanton-Hicks, Michael et al., "Complex Regional Pain Syndromes: Guidelines for Therapy", The Clinical Journal of Pain, 14:155-166 (1998).
Stevenson, P. Helen et al., "Cytotoxic and Migration Inhibitory Effects of Bisphosphonates on Macrophages", Calcif Tissue Int, 38:227-233 (1986).
Study: The Use of Zoledronic Acid to Complex Regional Pain Syndrome (Aclasta) sponsored by University of Sao Paulo General Hospital. 2012. Clinical Trials.gov. Accessed on Apr. 5, 2013 at http://clinicaltrials.gov/ct2/show/NCT01788176.
The University of Sheffield, Health & Economic impact of a new drug intervention for osteoporosis. http://www.sheffield.ac.uk/humanmetabolism/researchandyou/zoledronicacid, accessed Jun. 2014.
Tran, De Q.H., MD et al., "Treatment of complex regional pain syndrome: a review of the evidence—Traitement du syndrome de douleur regionale complexe: une revue des nonnees probantes", Can J. Anesth/J. Can Anesth, 57:149-166 (2010).
Adami, S. et al., "Bisphosphonate therapy of reflex sympathetic dystrophy syndrome", Annals of Rheumatic Diseases, 56:201-204 (1997).
Allen, Ginger et al., "Epidemiology of complex regional pain syndrome: a retrospective chart review of 134 patients", Pain® 80:539-544 (1999).
Alvarez-Lario, B. et al., "Acceptance of the different denominations for reflex sympathetic dystrophy", Ann Rheum Dis, 60:77-79 (2001).
Annual Mid-year Population Estimates, 2010, Office for National Statistics, Statistical Bulletin (2011).
Atkins, R.M. et al., "The Use of Dolorimetry in the Assessment of Post-Traumatic Algodystrophy of the Hand", British Journal of Rheumatology, 28:404-409 (1989).

Azari, Pari et al., "Efficacy and Safety of Ketamine in Patients with Complex Regional Pain Syndrome", CNS Drugs, 26(3):215-228 (2012).
Bertorelli et al., Nociceptin and the ORL-1 ligand [Phe1(CH2-NH)Gly2]nociceptin(1-13)NH2 exert anti-opioid effects in the Freund's adjuvant-induced arthritic rat model of chronic pain. British Journal of Pharmacology (1999) 128, 1252-1258.
Bickerstaff, D.R. et al., "Algodystrophy: An Under-Recognized Complication of Minor Trauma", British Journal of Rheumatology, 33:240-248 (1994).
Bickerstaff, D.R. et al., "Radiographic Changes in Algodystrophy of the Hand", Journal of Hand Surgery (British Volume) 16B:47-52 (1991).
Bingham III et al., Risedronate decreases biochemical markers of cartilage degradation but does not decrease symptoms or slow radiographic progression in patients with medical compartment osteoarthritis of the knee. Arthritis & Rheumatism, vol. 54, No. 11, 2006, 3494-3507.
Birklein, F. MD, et al., "The important role of neuropeptides in complex regional pain syndrome", Neurology, 57:2179-2184 (2001).
Bodde, Marlies I. et al., "Therapy-Resistant Complex Regional Pain Syndrome Type I: To Amputate or Not?", J. Bone Joint Surg. Am, 93:1799-805 (2011).
Bonabello, A. et al., "Analgesic effect of bisphosphonates in mice", Pain® 91:269-275 (2001).
Breuer, Brenda et al., "An Open-label Pilot Trial of Ibandronate for Complex Regional Pain Syndrome", Clin J Pain, 24(8):685-689 (2008).
Bruehl, Stephen Ph.D., "An Update on the Pathophysiology of Complex Regional Pain Syndrome", Anesthesiology, 113(3):713-25 (2010).
Brunner, Florian et al., "Biphosphonates for the therapy of complex regional pain syndrome I—Systematic review", European Journal of Pain, 13:17-21 (2009).
Cantatore FP, Acquista CA, Pipitone V. Evaluation of bone turnover and osteoclastic cytokines in early rheumatoid arthritis treated with alendronate. J Rheumatol 1999; 26: 2318-2323.
Cecchini, Marco G. et al., "Bisphosphonates in Vitro Specifically Inhibit, Amound the Hematopoietic Series, the Development of the Mouse Mononuclear Phagocyte Lineage", Journal of Bone and Mineral Research, 5 (10):1019-1027 (1990).
Chandler, Labeling of unit dose packages of drugs, Department of Pharmacy Policy, University of Kentucky Hospital, Chandler Medical Center, policy number: PH-04-06, 2009 (cited by examiner in co-pending U.S. Appl. No. 13/894,244).
Chauvineau et al. "What is the place of biphosphonates in the treatment of Complex Regional Pain Syndrome I?" Annales de readaptation de medecine physique 48 (2005) 150-157.
Classification of Chronic Pain. Descriptions of Chronic Pain Syndromes and Definitions of Pain Terms. Second Edition. (2002).
Commission Regulation (EC) No. 847/2000, Official Journal of the European Communities, (2000).
Committee for Orphan Medicinal Products (COMP) meeting report on the review of applications for orphan designation, European Medicines Agency, Sep. 2013.
Complex regional pain syndrome. NHS choices Feb. 27, 2012.
Complex Regional Pain Syndrome: Treatment Guidelines, Jun. 2006. Reflex Sympathetic Dystrophy Syndrome Association. Edited by R. Norman Harden.
Conte, et al., The Oncologist 2004:9(Supp 4):28-37.
Cremers, Serge C.L.M. et al., "Pharmacokinetics/Pharmacodynamics of Bisphosphonates", Clin Pharmacokinet, 44 (6):551-570 (2005).
CRPS: Biphosphonateshave yet to prove their usefulness. Douleurs Evaluation—Diagnostic—Traitement (2009) 10, 214-217.
Cullen et al., MER-101: A bioavailability study of various GIPET formulations in beagle dogs with intraduodenal cannulae. Poster Presentation, Nov. 2007.
De Castro et al., Zoledronic acid to treat complex regional pain syndrome type I in adult (case report). Rev. Dor. Sao Paulo, 2011, 12(1): 71-73.

(56) References Cited

OTHER PUBLICATIONS de Mos M, de Bruijn AGJ, Huygen FJPM, Dieleman JP, Stricker BHC, Sturkenboom MCJM. The incidence of complex regional pain syndrome: A population based study. Pain 2007; 129: 12-20.
de Mos M, Huygen FJPM, van der Hoeven-Borgman M, Dieleman JP, Stricker BHC, Sturkenboom MCJM. Outcome of the complex regional pain syndrome. Clin J Pain 2009; 25: 590-597.
Del Valle et al. "Spinal cord histopathological alterations in a patient with longstanding complex regional pain syndrome." Brain, Behavior and Immunity 23 (2009) 85-91.
Dielissen et al. "Amputation for Reflex Sympathetic Dystrophy." Jo Bone Joint Surg 1995:77-B: 270-3.
Drugs Orange Book Preface. Food and Drug Administration Center for Drug Evaluation and Research, 32nd Edition, accessed Mar. 6, 2014.
Drummond et al. "Reflex Sympathetic Dsytrophy: The Significance of Differing Plasma Catecholamine Concentrations in Affected and Unaffected Limbs." Brain (1991), 2025-2036.
E.U. Summary of product characteristics for Zometa and Aclasta (zoledronic acid), (2010).
English, A life of pain: woman chooses amputation to deal with painful disorder. Http://www.katu.com/news/loca.A-life-of-pain-woman-chooses-amputation-to-deal-with . . . Nov. 18, 2013.
EU Product Label for Zometa, accessed 2013.
Fay A, Abinun M. Current management of hereditary angio-oedema (C'1 esterase inhibitor deficiency). J Clin Pathol 2002; 55: 266-270.
FDA Approved medication Guide-Reclast (zoledronic acid) injection, Aug. 2011.
FDA Commissioner Margaret A. Hamburg Statement on Prescription Opioid Abuse (Apr. 3, 2014), available at: www.fda.gov/NewsEvents/Newsroom/PressAnnouncements/ucm391590.htm.
FDA Severe Pain with Osteoporosis drugs, Mar. 2008, FDA patient safety news: Show #73.
Finch PM, Knudsen L, Drummond PD. Reduction of allodynia in patients with complex regional pain syndrome: A double-blind placebo-controlled trial of topical ketamine. Pain 2009; 146: 18-25.
Forouzanfar T, Koke AJ, van Kleef M, Weber WE. Treatment of complex regional pain syndrome type I. Eur J Pain 2002; 6: 105-122.
Gangji V, Appelboom T. Analgesic effect of intravenous pamidronate on chronic back pain due to osteoporotic vertebral fractures. Clin Rheumatol 1999;—18: 266-267.
Garth T. Whiteside et al., DiPOA ([8-(3,3-Diphenyl-propyl)-4-oxo-1-phenyl-1,3,8-triazaspiro[4.5]dec-3-yl]-acetic Acid), a Novel, Systemically Available, and Peripherally Restricted MU Opioid Agonist with Antihyperalgesic Activity: II. In Vivo D Pharmacological Characterization in the Rat, 310 J. Pharmacol. & Exp. Ther. 793 (2004)).
Geertzen JH, Dijkstra PU, van Sonderen EL, Groothoff JW, ten Duis HJ, Eisma WH. Relationship between impairments, disability and handicap in reflex sympathetic dystrophy patients: a long-term follow-up study. Clin Rehabil 1998; 12:402-412.
Giles, Risedronate not an Effective Diesease Modifier in Knee Osteoarthritis. Arthritis News (website) 2006. Accessed at http://www.hopkinsarthritis.org/arthritis-news/risedronate-not-an-effective-disease-modifier-in-knee-osteoarthritis.
Goebel A, Barker CH, Turner-Stokes L et al. Complex regional pain syndrome in adults: UK guidelines for diagnosis, referral and management in primary and secondary care. London: RCP, 2012.
Goebel A, Leite MI, Yang L, Deacon R, Cendan CM, Fox-Lewis A, Vincent A. The passive transfer of immunoglobulin G serum antibodies from patients with longstanding Complex Regional Pain Syndrome. Eur J Pain 2011; 15: 504. e1-504.e6.
Goebel A. Complex regional pain syndrome in adults. Rheumatology (Oxford) 2011; 50:1739-1750.
Green JR, Rogers MJ. Pharmacologic profile of zoledronic acid: a highly potent inhibitor of bone resorption. Drug Dev Res 2002; 55: 210-224.
Guideline on the format and content of applications for designation as orphan medicinal products and on the transfer of designations from one sponsor to another, Jul. 9, 2007. ENTR/6283/00 Rev 3.

Guo et al., Substance P signaling contributes to the vascular and nociceptive abnormalities observed in a tibial fracture rat model of complex regional pain syndrome type I. Pain 108 (2004) 95-107.
Halvorson KG, Kubota K, Sevcik MA, Lindsay TH, Sotillo JE, Ghilardi JR, Rosol TJ, Boustany L, Shelton DL, Mantyh PW. A blocking antibody to nerve growth factor attenuates skeletal pain induced by prostate tumor cells growing in bone. Cancer Res 2005; 65: 9426-9435.
Hendren et al., A review of the differences between normal and osteoarthrisis articular cartilage in human knee and ankle joints, The Foot, vol. 19, Issue 3, Sep. 2009, pp. 171-176.
Henry McQuay, Opioids in pain management, 353 Lancet 2229, Abstract and 2229 (1999).
Henson P, Bruehl S. Complex regional pain syndrome: state of the art update. Curr Treat Options Cardiovasc Med 2010; 12: 156-167.
http://cancerguide.org/drugdosing.html, Page Created: 2000, last Updated: Sep. 22, 2000.
Huygen FJ, De Bruijn AG, De Bruin MT, Groeneweg JG, Klein J, Zijistra FJ. Evidence for local inflammation in complex regional pain syndrome type 1. Mediators Inflamm 2002; 11:47-51.
ICD-10-CM Tabular List of Diseases and Injuries 2012 p. 259-261,269-270. Source: The. National Center for Health Statistics (NCHS), Centers for Disease Control and Prevention.
Kemler MA, Barendse GA, van Kleef M, de Vet HC, Rijks CP, Furnee CA, van den Wildenberg FA. Spinal cord stimulation in patients with chronic reflex sympathetic dystrophy. N Engl J Med 2000; 343:618-624.
Kemler MA, de Vet HC, Barendse GA, van den Wildenberg FA, van Kleef M. Spinal cord stimulation for chronic reflex sympathetic dystrophy-five-year follow-up. N Engl J Med 2006; 354: 2394-2396.
Kemler MA, van de Vusse AC, van den Berg-loonen EM, Barendse GA, van Kleef M, Weber WE. HLA-001 associated with reflex sympathetic dystrophy. Neurology 1999; 53:1350-1351.
Kim et al, Analgesic effects of the non-nitrogen-containing bisphosphonates etidronate and clodronate, independent of antiresorptive effects on bone, European Journal of Pharmacology, vol. 699, Issues 1-3, 15, Jan. 2013, pp. 14-22 (Available online: Nov. 28, 2012).
Kingery et al., A substance P receptor (NK1) antagonist can reverse vascular and nociceptive abnormalities in a rat model of complex regional pain syndrome type II. Pain 104 (2003) 75-84.
Kirveskari E, Vartiainen NV, Gockel M, Forss N. Motor cortex dysfunction in complex regional pain syndrome. Clin Neurophysiol 2010; 121: 1085-1091.
Kohr D, Tschernatsch M, Schmitz K, Singh P, Kaps M, Schafer KH, Diener M, Mathies J, Matz 0, Kummer W, Maihofner C, FritzT, Birklein F, Blaes F. Autoantibodies in complex regional pain syndrome bind to a differentiation-dependent neuronal surface autoantigen. Pain. 2009; 143: 246-251.
Koman LA, Poehling GG, Smith BP, Smith TL, Chloros G. Chapter 59—Complex Regional Pain Syndrome. Green's Operative Hand Surgery, 6th ed.: Churchill Livingstone, 2010.
Kopterides P, Pikazis D, Koufos C. Successful treatment of SAPHO syndrome with zoledronic acid. Arthritis Rheum 2004; 50: 2970-2973.
Kramer HH, Eberle T, Uceyler N, Wagner I, Klonschinsky T, Muller LP, Sommer C, Birklein F. TNF-alpha in CRPS and 'normal' trauma-significant differences between tissue and serum. Pain 2011; 152: 285-290.
Kretzchmar A, Wiegel T, Al-Batran S, Hinrichs HF, Kindler M, Steck T, Illiger HJ, Heinemann V, Schmidt K, Haus U, Kirner A, Ehninger G. Rapid and sustained influence of intravenous zoledronic acid on course of pain and analgesics consumption in patients with cancer with bone metastases: A multicenter open-label study over 1 year Supportive Cancer Therapy 2007; 4: 203-210.
Laslett, Extended report: Zoledronic acid reduces knee pain and bone marrow lesions over 1 year: a randomized controlled trial. Ann. Rheum. Dis. 2012, 71: 1322-1328.
Leis et al. "Facilitated neurogenic inflammation in unaffected limbs of patients with complex regional pain syndrome." Neuroscience Letters 359 (2004) 163-166.

(56) References Cited

OTHER PUBLICATIONS

Leitha et al. "Pattern recognition in five-phase bone scintigraphy: diagnostic patterns of reflex sympathetic dystrophy in adults." European Journal of Nuclear Medicine vol. 23, No. 3, Mar. 1996.
Leonard et al., MER-101 Tablets: A pilot bioavailability study of a novel oral formulation of zoledronic acid. Poster Presentation, Oct. 2007.
Leonard et al., Safety Profile of Zoledronic acid in a novel oral formulation. Poster Presentation, Nov. 2009.
Leonard et al., Studies of bioavailability and food effects of MER-101 Zoledronic Acid Tablets in Postmenopausal Women. Poster Presentation, Oct. 2009.
Lewis et al. "Body perception disturbance: A contribution to pain in complex regional pain syndrome (CRPS)." Pain 133 (2007) 111-119.
Maihofner et al. "Cortical reorganization during recovery from complex regional pain syndrome." Neurology 2004; 63:693-701.
Maihofner et al. "Patterns of cortical reorganization in complex regional pain syndrome." Neurology 2003; 61:1707-1715.
Mailis-Gagnon et al. "Sympathectomy for neuropathic pain." Cochrane Database of Systematic Reviews 2002, Issue 1. Art CD002918, 2009.
Maksymowych et al. "A Six-Month Randomized, Controlled, Double-Blind, Dose-Response Comparison of Intravenous Pamidronate (60mg Versus 10mg) in the Treatment of Nonsteroidal Antiinflammatory Drug-Refractory Ankylosing Spondylitis." Arthritis & Rheumatism, vol. 46, No. 3, Mar. 2002, pp. 766-773.
Manicourt et al., Role of alendronate in therapy for postraumatic complex regional pain syndrome type 1 of the lower extremity arthirits rheum 2004.50:3690-3697.
Marinus et al. "Clinical features and pathophysiology of complex regional pain syndrome." Neurology vol. 10, Jul. 2011.
McHugh et al., MER-101-03, A multi center, phase II study to compare MER-101 20mg tablets to intravenous Zometa 4mg in prostate cancer patients. Poster Presentation, May 2009.
Mos et al. "Medical history and the onset of complex regional pain syndrome (CRPS)." Pain 139 (2009) 458-466.
Mos et al. "Outcome of the Complex Regional Pain Syndrome." Clin J Pain, vol. 25, No. 7, Sep. 2009.
Mos et al. "The association between ACE inhibitors and the complex regional pain syndrome: Suggestions for a neuro-inflammatory pathogenesis of CRPS." Pain 142 (2009) 218-224.
Mos et al. "The incidence of complex regional pain syndrome: A population-based study." Pain 129 (2007) 12-20.
Nagae et al., Acidic microenvironment created by osteoclasts causes bone pain associated with tumor colonization. J. Bone Miner. Metab. (2007) 25: 99-104.
Nagae et al., Osteoclasts play a part in pain due to the inflammation adjacent to bone. Bone 39 (2006) 1107-1115.
Nagakura et al., Allodynia and hyperalgesia in adjuvant-induced arthritic rats: time course of progression and efficacy of analgesics. The Journal of Pharmacology and Experimental Therapeutics 306: 490-497, 2003.
Nath et al. "Reflex Sympathetic Dystrophy." Hand Surgery Update 1. Volume 23, No. 3, Jul. 1996.
National Health Service, United Kingdom. Complex regional pain syndrome. NHS Choices, www.nhs.uk. Last reviewed May 23, 2012. Accessed Jul. 27, 2012.
U.S. Appl. No. 14/495,732, filed Jan. 26, 2015, Herriot Tabuteau, Antecip Bioventures II LLC.
U.S. Appl. No. 14/536,526, filed Jan. 28, 2015, Herriot Tabuteau, Antecip Bioventures II LLC.
U.S. Appl. No. 14/604,524, filed Jan. 23, 2015, Herriot Tabuteau, Antecip Bioventures II LLC.
U.S. Appl. No. 14/605,822, filed Jan. 26, 2015, Herriot Tabuteau, Antecip Bioventures II LLC.
U.S. Appl. No. 14/607,947, filed Jan. 28, 2015, Herriot Tabuteau, Antecip Bioventures II LLC.
U.S. Appl. No. 14/607,985, filed Jan. 28, 2015, Herriot Tabuteau, Antecip Bioventures II LLC.
U.S. Appl. No. 14/625,457, filed Feb. 18, 2015, Herriot Tabuteau, Antecip Bioventures II LLC.
U.S. Appl. No. 14/639,013, filed Mar. 4, 2015, Herriot Tabuteau, Antecip Bioventures II LLC.
U.S. Appl. No. 14/635,857, filed Mar. 2, 2015, Herriot Tabuteau, Antecip Bioventures II LLC.
Guideline Complex Regional Pain Syndrome type I, (2006).
Harden RN, Brush! S, Perez RS, Birklein F, Marinus J, Maihofner C, Lubenow T, Buvanendran A, Mackey S, Graciosa J, Mogilevski M, Ramsden C, Chont M, Vatine JJ. Validation of proposed diagnostic criteria (the "Budapest Criteria") for Complex Regional Pain Syndrome. Pain 2010; 150: 268-274.
Merskey H, Bogduk N. Classification of chronic pain: descriptions of chronic pain syndromes and definitions of pain terms, 2nd ed. Seattle, WA: IASP Press, 1994 p. 40-43.
Public summary of opinion on orphan designation. Zoledronic acid for the treatment of complex regional pain syndrome. European Medicines Agency, 2013.
U.S. Appl. No. 14/481,097, filed Sep. 9, 2014, Herriot Tabuteau, Antecip Bioventures II LLC.
U.S. Appl. No. 14/538,709, filed Nov. 11, 2014, Herriot Tabuteau, Antecip Bioventures II LLC.
U.S. Appl. No. 14/530,556, filed Oct. 31, 2014, Herriot Tabuteau, Antecip Bioventures II LLC.
U.S. Appl. No. 13/894,244, filed May 14, 2013, Herriot Tabuteau, Antecip Bioventures II LLC.
U.S. Appl. No. 13/894,252, filed May 14, 2013, Herriot Tabuteau, Antecip Bioventures II LLC.
U.S. Appl. No. 13/894,262, filed May 14, 2013, Herriot Tabuteau, Antecip Bioventures II LLC.
U.S. Appl. No. 13/894,274, field May 14, 2013, Herriot Tabuteau, Antecip Bioventures II LLC.
U.S. Appl. No. 14/106,291, filed Dec. 13, 2013, Herriot Tabuteau, Antecip Bioventures II LLC.
U.S. Appl. No. 14/279,196, filed May 15, 2014, Herriot Tabuteau, Antecip Bioventures II LLC.
U.S. Appl. No. 14/279,206, filed May 15, 2014, Herriot Tabuteau, Antecip Bioventures II LLC.
U.S. Appl. No. 14/279,213, filed May 15, 2014, Herriot Tabuteau, Antecip Bioventures II LLC.
U.S. Appl. No. 14/279,222, filed May 15, 2014, Herriot Tabuteau, Antecip Bioventures II LLC.
U.S. Appl. No. 14/279,226, filed May 15, 2014, Herriot Tabuteau, Antecip Bioventures II LLC.
U.S. Appl. No. 14/279,229, filed May 15, 2014, Herriot Tabuteau, Antecip Bioventures II LLC.
U.S. Appl. No. 14/279,232, filed May 15, 2014, Herriot Tabuteau, Antecip Bioventures II LLC.
U.S. Appl. No. 14/279,241, filed May 15, 2014, Herriot Tabuteau, Antecip Bioventures II LLC.
U.S. Appl. No. 14/279,236, filed May 15, 2014, Herriot Tabuteau, Antecip Bioventures II LLC.
U.S. Appl. No. 14/336,642, filed Jul. 21, 2014, Herriot Tabuteau, Antecip Bioventures II LLC.
U.S. Appl. No. 14/456,939, filed Aug. 11, 2014, Herriot Tabuteau, Antecip Bioventures II LLC.
U.S. Appl. No. 14/457,659, filed Aug. 12, 2014, Herriot Tabuteau, Antecip Bioventures II LLC.
Capello ZJ, et al., J Hand Surg Am. 2012; 37:288-296.
CRPS Orphan Drug Designation, zoledronic acid, Axome Therapeutics, May 6, 2013.
ISR & Written Opinion for PCT/US2014/050427, mailed Nov. 20, 2014.
Yasuhisa Abe et al., Improvement of Pain and Regional Osteoporotic Changes in the Foot and Ankle by Low-dose Bisphosphonate Therapy for Complex Regional Pain Syndrome Type I, J Med Case Reports. 2011;5(349).
Robinson et al, Efficacy of Pamidronate in Complex Regional Pain Syndrome Type I, American Academy of Pain Medicine 1526-2375, pp. 276-280,2004.
Rehman et al, P36 Treatment of reflex sympathetic dystrophy with intravenous pamidronate, Abstracts from the Bone and Tooth Society Meeting, Apr. 1991, p. 116.

(56) References Cited

OTHER PUBLICATIONS

Siminoski et al., Intravenous Pamidronate for Treatment of Reflex Sympathetic Dystrophy During Breast Feeding, Journal of Bone and Mineral Research vol. 15, No. 10, 2000.

Kubalek et al., Treatment of reflex sympathetic dystrophy with pamidronate: 29 cases, Rheumatology 2001; 40:1394-1397.

Maillefert et al., Treatment of refractory reflex sympathetic dystrophy with pamidronate, letters to the editor 1995, Correspondence to: Dr J F Maillefert, Service de Rhumatologie, Hopital General, 3 rue du Fb Raines, 21000 Dijon, France.

Devogelaer et al., Dramatic Improvement of Intractable Reflex Sympathetic Dystrophy Syndrome by Intravenous Infusions of the Second Generation Bisphosphonate APD., Poster presentation Jun. 1988, Tenth Annual Meeting of the American Society for Bone and Mineral Research Acadia Room, Bissonet Room and Exhibit Hall New Orleans Marriott Hotel Jun. 4-7, 1988.

Simm et al., The successful use of pamidronate in an 11-year-old girl with complex regional pain syndrome: Response to treatment demonstrated by serial peripheral quantitative computerised tomographic scan, Bone 46 (2010) 885-888.

Gremeaux et al., Complex Regional Pain Syndrome of the knee: early and good action of diphosphonates on pain and function, (English Abstract included) Annales de réadaptation et de médecine physique 50 (2007) 240-243.

Cortet et al., Treatment of Severe, Recalcitrant Reflex Sympathetic Dystrophy Assessment of Efficacy and Safety of the Second Generation Bisphosphonate Pamidronate, Clinical rheumatology, 1997, 16, 1:51-56.

Ying Wang et al., CXCL10 Controls Inflammatory Pain via Opioid Peptide-Containing Macrophages in Electroacupuncture, PLOS One, Apr. 2014, vol. 9, Issue 4, e94696.

Zhang Y, et al., Eur Spine J. 2008; 17:1289-1299.

Epstein et al., Update of Monthly Oral Bisphosphanate Therapy for the Treatment of Osteoporosis: Focus on Ibandronate 150 mg and Risedronate 150 mg, Current Medical Research and Opinion Journal, 25(12): 2951-2960, 2009.

* cited by examiner

THERAPEUTIC COMPOSITIONS COMPRISING IMIDAZOLE AND IMIDAZOLIUM COMPOUNDS

FIELD

Some embodiments relate to therapeutic compositions comprising substituted imidazoles and imidazoliums having multiple acidic groups.

SUMMARY

Pharmaceutical compositions comprising:

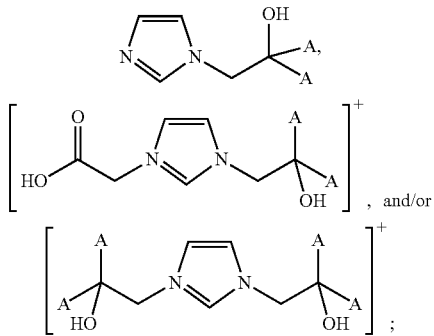

wherein each A is independently an acidic functional group, may be used for a number of medical purposes, such as treatment of undesirable conditions or diseases, including disease or conditions related to bone, cancer, and/or pain. In some embodiments, each A is $CO_2H$, $SO_3H$, $OSO_2$, or $PO_3H_2$.

Some embodiments include a dosage form, such as an oral dosage form, comprising a composition described herein.

Some embodiments include a method of treating a disease or condition related to bone, cancer, or pain, comprising administering a dosage form, such as an oral dosage form, comprising a composition described herein to a mammal in need thereof.

DETAILED DESCRIPTION

Preferably, pharmaceutical compositions comprising zoledronic acid, Compound 1, and/or Compound 2 (subject compositions), may be used for a number of medical purposes, such as treatment of undesirable conditions or diseases, including disease or conditions related to bone, cancer, and/or pain. This may be accomplished in many instances by administration of dosage forms, such as oral dosage forms, comprising a subject composition. Generally, an oral dosage form comprising a subject composition is administered orally to a mammal, such as a human being, at least once, to treat a disease or condition, such as disease or condition related to bone, cancer, or pain.

Compound 1

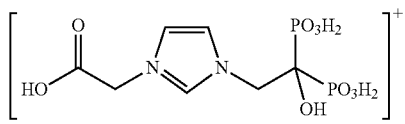

Compound 2

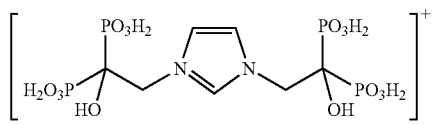

The term "treating" or "treatment" broadly includes any kind of treatment activity, including the diagnosis, cure, mitigation, or prevention of disease in man or other animals, or any activity that otherwise affects the structure or any function of the body of man or other animals.

An oral dosage form comprising a subject composition may be used to treat, or provide relief of, any type of pain including, but not limited to, inflammatory pain, arthritis pain, complex regional pain syndrome, lumbosacral pain, musculoskeletal pain, neuropathic pain, chronic pain, cancer-related pain, acute pain, postoperative pain, etc. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. In some embodiments, enhanced bioavailability of the zoledronic acid may be achieved in treating one of these conditions by administering a dosage form comprising a subject composition wherein zoledronic acid is in the form of a disodium salt. This may allow a reduced molar amount of the disodium salt to be used as compared to what would be used with the diacid form.

In some embodiments, the mammal being treated is not suffering from bone metastasis. In some embodiments, the mammal being treated is not suffering from cancer. In some embodiments, the mammal being treated is not suffering from osteoporosis.

For example, a subject composition may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc. In some embodiments, enhanced bioavailability of the zoledronic acid may be achieved in treating one of these conditions by administering a dosage form comprising a subject composition, wherein the zoledronic acid is in the form of a disodium salt. This may allow a reduced molar amount of the disodium salt of zoledronic acid to be used as compared to what would be used with the diacid form.

In some embodiments, a subject composition may also be administered orally to relieve neuropathic pain, including diabetic peripheral neuropathy, post-herpetic neuralgia, trigeminal neuralgia, monoradiculopathies, phantom limb pain, and central pain. Other causes of neuropathic pain include cancer-related pain, lumbar nerve root compression, spinal cord injury, post-stroke pain, central multiple sclerosis pain, HIV-associated neuropathy, and radio-therapy or chemo-therapy associated neuropathy. In some embodiments, enhanced bioavailability of the zoledronic acid may be achieved in treating one of these conditions by administering a dosage form comprising a subject composition, wherein the zoledronic acid is in the form of a disodium salt. This may allow a reduced molar amount of the disodium salt of zoledronic acid to be used as compared to what would be used with the diacid form.

In some embodiments, a subject composition may be administered orally to relieve inflammatory pain including musculoskeletal pain, arthritis pain, and complex regional pain syndrome. In some embodiments, enhanced bioavailability of the zoledronic acid may be achieved in treating one of these conditions by administering a dosage form comprising a subject composition in the form of a disodium salt. This may allow a reduced molar amount of the disodium salt to be used as compared to what would be used with the diacid form.

Examples of musculoskeletal pain include low back pain, pain associated with vertebral crush fractures, fibrous dysplasia, osteogenesis imperfecta, Paget's disease of bone, transient osteoporosis, and transient osteoporosis of the hip.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, a human being that is treated for an inflammatory condition such as arthritis by a subject composition has an age of about 10 years to about 90 years, about 20 years to about 80 years, about 30 years to about 75 years old, about 40 years to about 70 years, about 1 year to about 16 years, or about 80 years to about 95 years.

In some embodiments, a human being that is treated for an inflammatory condition such as arthritis by an oral dosage form of a subject composition has suffered from the arthritis for at least 1 month, at least 2 months, at least 6 months, or at least 1 year.

In some embodiments, the an inflammatory condition such as arthritis affects, a knee, an elbow, a wrist, a shoulder, or a hip.

In some embodiments, a subject composition may be administered orally to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component.

Complex regional pain syndrome is a debilitating pain syndrome. It is characterized by severe pain in a limb accompanied by edema, and autonomic, motor and sensory changes.

With respect to use of a subject composition for relieving pain associated with an inflammatory condition, relief of pain can be short-term, e.g. for a period of hours after administration of the dosage form, and/or relief of pain can be long-term, e.g. lasting for days, weeks, or even months after oral administration of a subject composition. In some embodiments, a mammal, such as a human being, experiences significant pain relief at least about 3 hours, at least about 6 hours, at least about 12 hours, at least about 24 hours, at least about 48 hours, at least about one week, at least about 2 weeks, or at least about 3 weeks after administration of an oral dosage form comprising a subject composition. In some embodiments, a mammal, such as a human being, experiences significant pain relief during at least part of the time from about 3 hours to about 2 weeks, about 3 hours to about 3 weeks, about 3 hours to about 24 hours, about 6 hours to about 2 weeks, or about 6 hours to about 24 hours, about 3 days to about 2 weeks, about 6 days to about 2 weeks, after administration of an oral dosage form comprising a subject composition.

With respect to the treatment of any condition recited herein, in some embodiments a first oral dosage form comprising a subject composition is administered and a second oral dosage form comprising a subject composition is administered. The timing of the administration of the two dosage forms may be such that, with respect to the first oral dosage form, the second oral dosage with respect to the first oral dosage form, the second oral dosage form is administered at $5 \times T_{max}$ or greater (e.g., if $T_{max}$ is 1 hour, at 5 hours or later), at least $10 \times T_{max}$ or greater, at least about $15 \times T_{max}$ or greater, at least about $20 \times T_{max}$ or greater, at least about $50 \times T_{max}$ or greater, or at least about $200 \times T_{max}$ or greater, wherein $T_{max}$ is the time of maximum plasma concentration of zoledronic acid after administration the first oral dosage form.

Some embodiments include treatment of a condition recited herein, such as inflammatory pain, arthritis, or complex regional pain syndrome, wherein the treatment comprises either: administering only one dosage form to a mammal to treat the condition, or administering a first dosage form to the mammal, followed by administering a second dosage form to the mammal. If two or more dosage forms are administered, in some embodiments, the second oral dosage form is administered before the maximum pain relieving effect of the first oral dosage form is achieved, or before a peak in the pain relieving effect of the first oral dosage form is experienced, by a mammal receiving the dosage form. In some embodiments, the second oral dosage form is administered before an observable pain relieving effect is achieved. In some embodiments, the second dosage form is administered about 12 hours to about 60 days, about 24 hours to about 28 days, about 24 hours to about 7 days, about 24 hours to about 14 days, or about 24 hours to about 21 days, after the first dosage form is administered.

Some embodiments include treatment of a condition recited herein, such as inflammatory pain, arthritis, or complex regional pain syndrome, wherein the treatment comprises administering a first dosage form to the mammal, followed by administering a second dosage form to the mammal, wherein the second dosage form is administered after the maximum pain relieving effect of the first oral dosage form is achieved, and the second oral dosage form is administered while the mammal is still experiencing pain relief from the first oral dosage form, or while the pain relieving effect from the first oral dosage form is observable. In some embodiments, the second dosage form is administered about 12 hours to about 60 days, about 24 hours to about 28 days, about 24 hours to about 7 days, about 24 hours to about 14 days, or about 24 hours to about 21 days, after the first dosage form is administered.

A subject composition may also be administered orally to relieve cancer-related pain, including pain associated with multiple myeloma and bone metastases from solid tumors. In some embodiments, a subject composition is used to treat pain that is not cancer-related pain. For example, a subject composition may be used to treat pain that is not associated with multiple myeloma, bone metastasis from solid tumors, hypercalcemia of malignancy, giant cell tumor of bone, blood cancers or leukemias, or solid tumors or cancers. In some embodiments, enhanced bioavailability of the zoledronic acid may be achieved in treating one of these conditions by administering a subject composition. This may allow a reduced molar amount of the disodium salt to be used as compared to what would be used with the diacid form.

In addition to relieving pain, oral administration of a subject composition may also be useful to treat diseases or conditions that may or may not include a pain component. For example, a subject composition may be useful to treat any of the pain conditions or types of conditions listed above, including treatment that does not simply relieve the pain of those conditions, and treatment that is carried out in such a way that the condition is treated without pain relief occurring. In addition to any pain relief a subject composition may or may not provide, a subject composition may be used to treat a disease or condition such as a metabolic disease or condition; an inflammatory disease or condition, including an inflammatory disease or condition that is not associated with pain; a cancer disease or condition; a neurological disease or condition; etc. In some embodiments, enhanced bioavailability of the zoledronic acid may be achieved in treating one of these conditions by administering a dosage form comprising a subject composition. This may allow a reduced molar amount of the disodium salt to be used as compared to what would be used with the diacid form.

In some embodiments, oral administration of a subject composition may also be useful to treat complex regional pain syndrome, rheumatoid arthritis, osteoarthritis, erosive osteoarthritis, axial spondyloarthritis including ankylosing spondylitis, acute vertebral crush fracture, fibrous dysplasia, SAPHO syndrome, osteoporosis, transient osteoporosis, or transient osteoporosis of the hip. In some embodiments, enhanced bioavailability of the zoledronic acid may be achieved in treating one of these conditions by administering a dosage form comprising a subject composition, wherein the zoledronic acid is in a disodium salt form. This may allow a reduced molar amount of the disodium salt to be used as compared to what would be used with the diacid form.

In some embodiments, oral administration of a subject composition may also be useful to treat hypercalcemia of malignancy, multiple myeloma, bone metastases from solid tumors, Paget's disease of bone, giant cell tumor of bone, blood cancers or leukemias, or solid tumors or cancers. In some embodiments, enhanced bioavailability of the zoledronic acid may be achieved in treating one of these conditions by administering a dosage form comprising a subject composition, wherein the zoledronic acid is in the form of a disodium salt. This may allow a reduced molar amount of the disodium salt to be used as compared to what would be used with the diacid form.

Zoledronic acid has the structure shown below, and is also referred to as zoledronate.

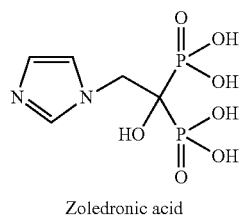

Zoledronic acid

Unless otherwise indicated, any reference to a compound herein, such as a subject composition, zoledronic acid, Compound 1 or Compound 2, by structure, name, or any other means, includes pharmaceutically acceptable salts, such as the disodium salt; alternate solid forms, such as polymorphs, solvates, hydrates, etc.; tautomers; or any other chemical species that may rapidly convert to a compound described herein under conditions in which the compounds are used as described herein.

In some embodiments, zoledronic acid is in a composition or dosage form comprising a salt form, such as a salt of a dianion of zoledronic acid. In some embodiments, zoledronic acid is administered in a dosage form comprising a disodium salt form of zoledronic acid. In some embodiments, zoledronic acid is administered as a subject composition. In some embodiments, zoledronic acid is administered in a sodium salt form, such as a monosodium salt, a disodium salt, a trisodium salt, etc. In some circumstances, use of the disodium salt may be desirable. For example, the disodium salt is much more soluble in water than the diacid form. As a result, in some processes, the disodium salt can be easier to work with than the diacid form. Additionally, the sodium salt may be more bioavailable and/or more rapidly absorbed when taken orally as compared to the diacid form.

Examples of salts of Compound 1 are shown below:

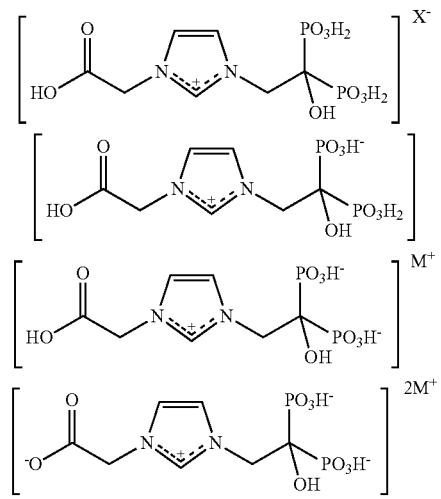

wherein $X^-$ is any suitable anion, e.g. F, Br, Cl$^-$, I$^-$, acetate, etc.; and $M^+$ is any suitable cation, e.g. Na$^+$, K$^+$, NH$_4^+$, etc.

In some embodiments, Compound 1 is administered in a dosage form comprising a salt form, such as a salt of a dianion of Compound 1. In some embodiments, Compound 1 is administered in a dosage form comprising a disodium salt form of Compound 1. In some embodiments, Compound 1 is administered in a sodium salt form, such as a monosodium salt, a disodium salt, a trisodium salt, etc. In some circumstances, use of the disodium salt may be desirable.

Compound 1 can be present in any amount, such as less than about 100% w/w, less than about 50% w/w, less than about 20% w/w, less than about 10% w/w, less than about 1% w/w, less than about 0.1% w/w, less than about 0.07% w/w, less than about 0.05% w/w, less than about 0.04% w/w, less than about 0.03% w/w, less than about 0.02% w/w; and/or greater than 0% w/w, at least about 0.00000001% w/w, at least about 0.000001% w/w, or at least about 0.00001% w/w, based upon the total amount of zoledronic acid, Compound 1, and Compound 2 present in the composition.

Examples of salts of Compound 2 are shown below:

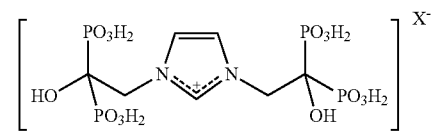

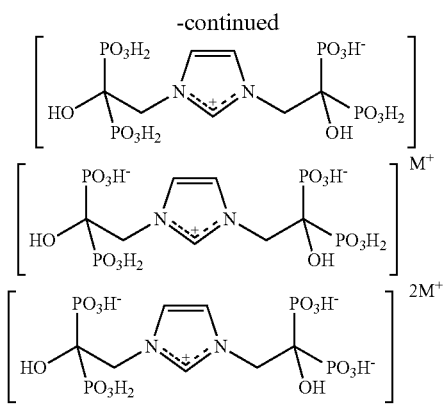

wherein X⁻ is any suitable anion, e.g. F⁻, Br⁻, Cl⁻, I⁻, acetate, etc.; and M⁺ is any suitable cation, e.g. Na⁺, K⁺, $NH_4^+$, etc.

In some embodiments, Compound 2 is administered in a dosage form comprising a salt form, such as a salt of a dianion of Compound 2. In some embodiments, Compound 2 is administered in a dosage form comprising a disodium salt form of Compound 2. In some embodiments, Compound 2 is administered in a sodium salt form, such as a monosodium salt, a disodium salt, a trisodium salt, etc. In some circumstances, use of the disodium salt may be desirable.

Compound 2 can be present in any amount, such as less than about 100% w/w, less than about 50% w/w, less than about 20% w/w, less than about 10% w/w, less than about 1% w/w, less than about 0.3%, less than about 0.2%, less than 0.1% w/w, less than about 0.08% w/w, less than about 0.07% w/w, less than about 0.05% w/w, less than about 0.04% w/w, less than about 0.03% w/w, less than about 0.02% w/w; and/or greater than 0% w/w, at least about 0.00000001% w/w, at least about 0.000001% w/w, or at least about 0.00001% w/w, based upon the total amount of zoledronic acid, Compound 1, and Compound 2 present in the composition.

In some embodiments, Compound 1 and Compound 2 are present in an amount that is less than 0.1% w/w, The oral bioavailability of zoledronic acid in a subject composition may be enhanced by orally administering the zoledronic acid in the disodium salt form. For example, the bioavailability of zoledronic acid may be improved by at least about 10%, at least about 20%, at least about 30%, at least about 50%, and/or up to about 100%, or up to about 200%, as compared to administration of zoledronic acid in the diacid form.

Because of the improved bioavailability of the disodium salt a dosage form may contain, or a mammal, such as a human being, may receive, on a molar basis, less of the disodium salt form of zoledronic acid than would otherwise be administered of the diacid form of zoledronic acid. For example, a dosage form may contain, or a mammal may receive, at least about 10 mole % less, at least about 20 mole % less, at least about 40 mole % less, at least about 50 mole % less, and/or up to about 90 mole % less or 95 mole % less, of the disodium salt form as compared to the amount of the diacid form of zoledronic acid that would otherwise be administered, such as a molar amount that would be administered of zoledronic acid in the diacid form in order to achieve the same plasma levels of zoledronic acid.

In some embodiments, a dosage form contains, or a mammal (such as a human being) is administered, an amount of the disodium salt form of zoledronic acid, on a molar basis, that has a value of about $0.8 n_d$ to about $1.2 n_d$ or about $0.9 n_d$ to about $1.1 n_d$, wherein:

$$n_d = (b_a/b_d)(n_a)$$

wherein $b_a$ is the bioavailability of the diacid form, $b_d$ is the bioavailability of the disodium salt form, and $n_a$ is the number of moles of the diacid that would be administered in a dosage form containing the diacid form of zoledronic acid. For example, if the diacid form has a bioavailability ($b_a$) of 0.01 and the disodium salt form has a bioavailabity ($b_d$) of 0.015, and a dosage form would normally contain 0.001 moles of the diacid, $n_d$ would be (0.01/0.015)(0.001 moles), or about 0.00067 moles. In some embodiments, the disodium salt is administered in an amount that has a value of about $n_d$.

With respect to oral dosage forms comprising a reduced molar amount of the disodium salt of zoledronic acid as compared to the diacid form of zoledronic acid, in some embodiments, the bioavailability of the zoledronic acid in the disodium salt form is sufficiently high that, if the drug is administered to a mammal, at least as much zoledronic acid is present in the blood of the mammal as would be present if zoledronic acid were administered in the diacid form.

With respect to oral dosage forms comprising the disodium salt form of zoledronic acid, in some embodiments, the disodium salt form is present in a lower molar amount than would be present if the zoledronic acid were in the diacid form; and the zoledronic acid in the disodium salt form has an improved bioavailability as compared to the zoledronic acid in the diacid form to the extent that the lower molar amount of the disodium salt in the dosage form does not reduce the amount of zoledronic acid delivered to the plasma of a mammal.

In some embodiments, the zoledronic acid in the disodium salt form is present in an amount such that the oral dosage form provides an area under the plasma concentration curve of zoledronic acid of about 4 ng·h/mL to about 2000 ng·h/mL to the mammal each time the zoledronic acid in the disodium salt is administered.

In some embodiments, the zoledronic acid in the disodium salt form is present in an amount such that the oral dosage form provides an area under the plasma concentration curve of zoledronic acid of about 100 ng·h/mL to about 2000 ng·h/mL, about 100 ng·h/mL to about 1000 ng·h/mL, about 500 ng·h/mL to about 1000 ng·h/mL, or about 500 ng·h/mL to about 700 ng·h/mL in the mammal to which the dosage form is administered. This amount may be suitable for administration of the oral dosage form about every 3 to 4 weeks.

In some embodiments, the zoledronic acid in the disodium salt form is present in an amount such that the oral dosage form provides an area under the plasma concentration curve of zoledronic acid of about 20 ng·h/mL to about 700 ng·h/mL, about 50 ng·h/mL to about 500 ng·h/mL, or about 100 ng·h/mL to about 200 ng·h/mL, in the mammal to which the dosage form is administered. This amount may be suitable for weekly administration of the oral dosage, or for administration of 3 to 5 individual dosages during a month. The individual dosages could be given at regular intervals, given during the first week, or at any other schedule that provides 3 to 5 dosages during the month.

In some embodiments, the zoledronic acid in the disodium salt form is present in an amount such that the oral dosage form provides an area under the plasma concentration curve of zoledronic acid of about 4 ng·h/mL to about 100 ng·h/mL, about 10 ng·h/mL to about 50 ng·h/mL, or about 10 ng·h/mL to about 30 ng·h/mL, in the mammal to which the dosage form is administered. This amount may be suitable for daily administration of the oral dosage form.

Oral administration of a subject composition, particularly oral administration of a subject composition comprising the disodium salt form of zoledronic acid, can result in more sustained plasma levels of the drug as compared to parenteral modes of administration, such intravenous or subcutaneous. For example, the amount of zoledronic acid in the plasma can be significantly higher for oral administration of the disodium salt about 12 hours, about 24 hours, about 36 hours, about 48 hours, or about 72 hours, or longer, after administration.

In some embodiments, zoledronic acid in an orally administered subject composition has a 12 hour sustained plasma factor of about 5 or higher or about 10 or higher, such as about 10 to about 100, about 20 to about 50, or about 30 to about 40.

In some embodiments, zoledronic acid in an orally administered subject composition has a 24 hour sustained plasma factor of about 3 or higher or about or higher, such as about 5 to about 50, about 10 to about 20, or about 12 to about 15.

In some embodiments, zoledronic acid in an orally administered subject composition has a 36 hour sustained plasma factor of about 3 or higher or about 5 or higher, such as about 5 to about 30, about 5 to about 15, or about 9 to about 13.

In some embodiments, zoledronic acid in an orally administered subject composition has a 48 hour sustained plasma factor of about 3 or higher or about 5 or higher, such as about 5 to about 30, about 5 to about 15, or about 8 to about 12.

In some embodiments, zoledronic acid in an orally administered subject composition has a 72 hour sustained plasma factor of about 3 or higher or about 5 or higher, such as about 5 to about 30, about 5 to about 15, or about 8 to about 12.

In some embodiments, zoledronic acid in an orally administered subject composition has a 24 hour sustained plasma level factor of about 1 or higher, such as about 1 to about 10, about 1 to about 5, about 3 to about 5, or about 3 to about 4. In some embodiments, a zoledronic acid in an orally administered subject composition has a 12 hour sustained plasma level factor, a 24 hour sustained plasma level factor, 36 hour sustained plasma level factor, a 48 hour sustained plasma level factor, or a 72 hour sustained plasma level factor that is higher, such as at least 1.2 times, at least about 2 times, at least about 5 times, about 1.2 times to about 20 times, about 2 times to about 15 times, about 5 times to about 10 times, or about 8 to about 15 times that of intravenously administered zoledronic acid. A "sustained plasma level factor," $p_f$, is determined by the equation:

$$p_f = 1000(C_t/C_{max})$$

wherein $C_{max}$ is the maximum plasma concentration of zoledronic acid after it is administered and $C_t$ is the plasma concentration of zoledronic acid at the time of interest, such as 24 hours. For parenteral administration, the $C_{max}$ can be about the $C_0$, or the concentration right after injection of the entire amount of the drug into the body. Sustained plasma level factors can also be obtained for other times, such as 48 hours, by using the plasma concentration of zoledronic acid for $C_t$ in the equation above. For example, if the maximum plasma level of zoledronic acid after administration is 1000 ng/mL and the plasma level of zoledronic acid at 24 hours is 1 ng/mL, the 24 hour sustained plasma level factor is 1.

In some embodiments, the disodium salt form of zoledronic acid provides an enhancement to bioavailability, as compared to the diacid form of zoledronic acid, which adds to any enhancement to bioavailability provided by any bioavailability-enhancing agents in the dosage form. In some embodiments, the disodium salt form of zoledronic acid provides an enhancement to bioavailability, as compared to the diacid form of zoledronic acid, which is greater than any enhancement to bioavailability provided by any bioavailability-enhancing agents in the dosage form. In some embodiments, the disodium salt form of zoledronic acid may be administered in a dosage form that is substantially free of bioavailability-enhancing agents.

In some embodiments, a dosage form comprising a subject composition is a solid.

In some embodiments, a subject composition is used to treat an inflammatory condition.

In some embodiments, a subject composition is used to treat arthritis.

In some embodiments, a subject composition is used to treat complex regional pain syndrome.

In some embodiments, zoledronic acid is in a form that has an aqueous solubility, meaning the solubility in water, greater than 1% (w/v), about 5% (w/v) to about 50% (w/v), about 5% (w/v) to about 20% (w/v), about 10% (w/v) to about 15% (w/v), or about 12% (w/v) to about 13% (w/v).

The disodium salt form of zoledronic acid can be more compressible than the diacid form of zoledronic acid. This can make it easier for a dosage form to have a desired hardness. It can also make it easier to increase the drug load, so that a smaller tablet can be given for a given dosage strength. In some embodiments, a solid dosage form of zoledronic acid, such as the diacid form of zoledronic acid or the disodium salt form of zoledronic acid, can have a hardness of about 5 kPa to about 20 kPa or about 5 kPa to about 14 kPa.

Zoledronic acid, and Compound 1 and/or Compound 2, may be combined with a pharmaceutical carrier selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

A subject composition may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, zoledronic acid, and Compound 1 and/or Compound 2, may be administered as the only active agents in a pharmaceutical composition, or they can be used in combination with other therapeutically active ingredients.

A subject composition may be administered to a human patient in a variety of forms adapted to the chosen route of administration, e.g., orally, rectally, or parenterally. Parenteral administration in this respect includes, but is not limited to, administration by the following routes: pulmonary, intrathecal, intraarticular, intravenous, intramuscular, subcutaneous, intraocular, intrasynovial, transepithelial including transdermal, sublingual and buccal; topically; nasal inhalation via insufflation; and rectal systemic.

The effective amount of a subject composition will vary depending on various factors known to the treating physicians, such as the severity of the condition to be treated, route of administration, formulation and dosage forms, physical characteristics of the bisphosphonate compound used, and age, weight and response of the individual patients.

The amount of zoledronic acid in a subject composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of zoledronic acid.

Some solid subject compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 75% (w/w), about 70% (w/w) to about 80% (w/w), or about 80% (w/w) to about 90% (w/w) of zoledronic acid.

Any suitable amount of zoledronic acid may be used. Some solid or liquid oral dosage forms, or units of oral dosage forms comprising a subject composition (referred to collectively herein as "oral dosage form(s)") may contain about 0.005 mg to about 20 mg, about 0.1 mg to about 10 mg, about 0.5 mg to about 10 mg, about 0.2 mg to about 5 mg, about 1 mg to about 500 mg, about 1 mg to about 50 mg, about 10 mg to about 250 mg, about 100 mg to about 300 mg, about 20 mg to about 200 mg, about 20 mg to about 150 mg, about 30 mg to about 100 mg, about 1 mg to about 1,000 mg, about 10 mg to about 50 mg, about 10 mg to about 300 mg, about 10 mg to about 150 mg, about 10 mg to about 100 mg, about 40 mg to about 150 mg, about 10 mg to about 600 mg, about 40 mg to about 600 mg, about 40 mg to about 2000 mg, about 40 mg to about 800 mg, about 25 mg to about 800 mg, about 30 mg to about 800 mg, about 10 mg to about 500 mg, about 50 mg to about 150 mg, about 50 mg, about 100 mg, about 50 mg to about 500 mg, about 100 mg to about 2000 mg, about 300 mg to about 1500 mg, about 200 mg to about 1000 mg, about 100 mg to about 500 mg, or about 150 mg of zoledronic acid, or any amount of zoledronic in a range bounded by, or between, any of these values. In some embodiments, the oral dosage form is administered daily, weekly, monthly, every two or three months, once a year, or twice a year.

In some embodiments, an oral dosage form may contain about 10 mg/m$^2$ to about 20 mg/m$^2$, about 15 mg/m$^2$ to about 20 mg/m$^2$, about 18 mg/m$^2$, about 80 mg/m$^2$ to about 150 mg/m$^2$, about 90 mg/m$^2$ to about 150 mg/m$^2$, about 100 mg/m$^2$ to about 150 mg/m$^2$ of zoledronic acid, or any amount of zoledronic in a range bounded by, or between, any of these values. All dosage ranges or amounts expressed in mg/m$^2$ are based upon the body surface area of the mammal.

In some embodiments the daily or dose of zoledronic acid is about 0.005 mg to about 20 mg, about 0.1 mg to about 10 mg, about 0.5 mg to about 10 mg, about 0.2 mg to about 5 mg, or any amount of zoledronic acid in a range bounded by, or between, any of these values. In some embodiments, the daily oral dose of zoledronic acid is less than about 35 mg/m$^2$, less than about 30 mg/m$^2$, less than about 25 mg/m$^2$, about 1 mg/m$^2$ to about 35 mg/m$^2$, about 1 mg/m$^2$ to about 30 mg/m$^2$, about 1.5 mg/m$^2$ to about 25 mg/m$^2$, about 1.8 mg/m$^2$ to about 20 mg/m$^2$, about 10 mg/m$^2$ to about 20 mg/m$^2$, about 10 mg/m$^2$ to about 30 mg/m$^2$, about 15 mg/m$^2$ to about 20 mg/m$^2$, about 18 mg/m$^2$, or any amount of zoledronic acid in a range bounded by, or between, any of these values.

In some embodiments the weekly oral dose of zoledronic acid is about 1 mg to about 1000 mg, about 1 mg to about 500 mg, about 10 mg to about 250 mg, about 100 mg to about 300 mg, about 10 mg to about 100 mg, about 10 mg to about 150 mg, about 10 mg to about 100 mg, about 10 mg to about 300 mg, about 20 mg to about 150 mg, or about 30 mg to about 100 mg. In some embodiments, the weekly oral dose of zoledronic acid is less than about 250 mg/m$^2$, less than about 200 mg/m$^2$, less than about 175 mg/m$^2$, about 6 mg/m$^2$ to about 250 mg/m$^2$, about 10 mg/m$^2$ to about 210 mg/m$^2$, about 10 mg/m$^2$ to about 170 mg/m$^2$, about 4 mg/m$^2$ to about 140 mg/m$^2$, about 100 mg/m$^2$ to about 140 mg/m$^2$, about 126 mg/m$^2$, or any amount of zoledronic acid in a range bounded by, or between, any of these values. The weekly oral dose may be given as a single dose, given once during the week, or may be given in 2, 3, 4, 5, 6, or 7 individual doses during the week.

In some embodiments, the monthly dose of zoledronic acid, or the amount of zoledronic acid that is administered over a period of a month, is about 5000 mg or less, about 4000 mg or less, about 3000 mg or less, about 2000 mg or less, about 1000 mg or less, about 700 mg or less, about 600 mg or less, about 1 mg to about 4,000 mg, about 1 mg to about 1,000 mg, about 10 mg to about 1000 mg, about 50 mg to about 1000 mg, about 10 mg to about 600 mg, about 40 mg to about 600 mg, about 50 mg to about 600 mg, or about 100 mg to about 600 mg, about 40 mg to about 2000 mg, about 40 mg to about 800 mg, about 50 mg to about 800 mg, or about 100 mg to about 800 mg, about 40 mg to about 1000 mg, about 50 mg to about 1000 mg, or about 100 mg to about 1000 mg, or any monthly dose in a range bounded by, or between, any of these values. In some embodiments, the monthly oral dose of zoledronic acid is less than about 1000 mg/m$^2$, less than about 800 mg/m$^2$, less than about 600 mg/m$^2$, about 10 mg/m$^2$ to about 1000 mg/m$^2$, about 50 mg/m$^2$ to about 800 mg/m$^2$, about 70 mg/m$^2$ to about 700 mg/m$^2$, about 100 mg/m$^2$ to about 700 mg/m$^2$, about 100 mg/m$^2$ to about 600 mg/m$^2$, about 50 mg/m$^2$ to about 200 mg/m$^2$, about 300 mg/m$^2$ to about 600 mg/m$^2$, about 450 mg/m$^2$ to about 600 mg/m$^2$, about 300 mg/m$^2$ to about 1000 mg/m$^2$, about 400 mg/m$^2$ to about 1000 mg/m$^2$, about 500 mg/m$^2$ to about 1000 mg/m$^2$, about 400 mg/m$^2$ to about 700 mg/m$^2$, about 500 mg/m$^2$ to about 600 mg/m$^2$, about 540 mg/m$^2$, or any amount of zoledronic acid in a range bounded by, or between, any of these values. A monthly dose may be given as a single dose, or as two or more individual doses administered during the month. In some embodiments, the monthly dose is administered in 2 or 3 weekly doses. In some embodiments, the monthly dose is administered in 4 or 5 weekly doses. In some embodiments, the monthly dose is administered in 28 to 31 daily doses. In some embodiments, the monthly dose is administered in 5 to 10 individual doses during the month. The monthly dose may be administered for only 1 month, or may be repeatedly administered for 2 or more months.

A subject composition, may be administered in combination with about 0.1 mg to about 10 mg of zoledronic acid, or a salt thereof, administered parenterally, such as intravenously. In some embodiments, about 50 mg, about 100 mg, or about 150 mg of the disodium salt of zoledronic acid is administered orally in combination with 1 mg parenteral, such as intravenous, zoledronic acid. In some embodiments the parenteral dose of zoledronic acid is about 0.25 mg to about 25 mg, about 0.25 mg to about 10 mg, or about 0.5 mg to about 7.5 mg.

With respect to oral administration of a subject composition, for the treatment of pain associated with inflammation, arthritis, CRPS, or any other condition recited herein, it may helpful if the mammal or human being to which a subject composition is administered does not eat food or drink beverage, (other than any water required to swallow the oral dosage form) for at least about 1 hour, at least about 2 hours, at least about 4 hours, at least about 6 hours, at least about 8 hours, at least about 10 hours, or at least about 12 hours before the subject composition is administered. It may also be helpful if the mammal or human being to which the subject composition is administered does not eat food or drink beverage for at least about 30 minutes, at least about 1 hour, at least about 2 hours, at least about 3 hours, or at least about 4 hours after the subject composition is administered. In some embodiments, a human being to which the subject composition is administered avoids lying down, or remains upright or sits upright, for at least about 30 minutes or about 1 hour after receiving a dosage form containing the subject composition. Avoiding food or beverage before or after oral administration of a subject composition can improve the bioavailability of the zoledronic acid.

The oral bioavailability of zoledronic acid in a dosage form can vary. Some dosage forms may have ingredients added to enhance the bioavailability. However, bioavailability enhancement is not necessary for an oral dosage form to be effective. In some embodiments, the dosage form is substantially free of bioavailability-enhancing agents. In some embodiments, an oral dosage form may have an oral bioavailability of zoledronic acid of about 0.01% to about 10%, about 0.1% to about 7%, about 0.1% to about 5%, etc. Without ingredients or other methods to enhance bioavailability, zoledronic acid typically has a low bioavailability in an oral dosage form. In some embodiments, the oral bioavailability of zoledronic acid is unenhanced or substantially unenhanced. For example, the oral bioavailability of zoledronic acid can be about 0.01% to about 5%, about 0.01% to about 4%, about 0.1% to about 3%, about 0.1% to about 2%, about 0.2% to about 2%, about 0.2% to about 1.5%, about 0.3% to about 1.5%, about 0.3% to about 1%, about 0.1% to about 0.5%, about 0.3% to about 0.5%, about 0.5% to about 1%, about 0.6% to about 0.7%, about 0.7% to about 0.8%, about 0.8% to about 0.9%, about 0.9%, about 1% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.8%, about 1.8% to about 2%, about 1% to about 3%, about 1% to about 2%, about 1.5% to about 3%, about 2% to about 3%, or about 1.8% to about 2.3%.

Some embodiments include an oral dosage form comprising a subject composition, wherein the oral bioavailability of zoledronic acid in the dosage form is from about 0.01% to about 10%.

In some embodiments, the or bioavailability of zoledronic acid in a dosage form is about 0.01% to about 5%.

In some embodiments, the or bioavailability of zoledronic acid in a dosage form is about 0.1% to about 7%.

In some embodiments, the oral bioavailability of zoledronic acid in a dosage form is about 0.1% to about 5%.

In some embodiments, the or bioavailability of zoledronic acid in a dosage form is about 0.1% to about 3%.

In some embodiments, the or bioavailability of zoledronic acid in a dosage form is about 0.1% to about 2%.

In some embodiments, the oral bioavailability of zoledronic acid in a dosage form is about 0.2% to about 2%.

In some embodiments, the or bioavailability of zoledronic acid in a dosage form is about 0.2% to about 1.5%.

In some embodiments, the oral bioavailability of zoledronic acid in a dosage form is about 0.3% to about 1.5%.

In some embodiments, the oral bioavailability of zoledronic acid in a dosage form is about 0.3% to about 1.0%.

In some embodiments, an oral dosage form comprises about 10 mg to about 300 mg of zoledronic acid, and is administered daily for about 2 to about 15 consecutive days. This regimen may be repeated once monthly, once every two months, once every three months, once every four months, once every five months, once every six months, once yearly, or once every two years.

In some embodiments, an oral dosage form comprises about 10 mg to about 150 mg or about 10 mg to about 100 mg of zoledronic acid, and is administered daily for about 2 to about 15 consecutive days. This regimen may be repeated once monthly, once every two months, once every three months, once every four months, once every five months, once every six months, once yearly, or once every two years.

In some embodiments, an oral dosage form comprises about 10 mg to about 150 mg or about 10 mg to about 100 mg of zoledronic acid, and is administered daily for about 5 to about 10 consecutive days. This regimen may be repeated once monthly, once every two months, once every three months, once every four months, once every five months, once every six months, once yearly, or once every two years.

In some embodiments, an oral dosage form comprises about 40 mg to about 150 mg of zoledronic acid, and is administered daily for about 5 to about 10 consecutive days. This regimen may be repeated once monthly, once every two months, once every three months, once every four months, once every five months, once every six months, once yearly, or once every two years.

In some embodiments, the oral zoledronic acid may be administered as one dose of about 100 mg to about 2000 mg. In some embodiments, the oral zoledronic acid may be administered as one dose of about 300 mg to about 1500 mg. In some embodiments, the oral zoledronic acid may be administered as one dose of about 200 mg to about 1000 mg. The dose of zoledronic acid may be administered in a single or divided dose.

Zoledronic acid in combination with Compound 1 and/or Compound 2 may be formulated for oral administration, for example, with an inert diluent or with an edible carrier, or it may be enclosed in hard or soft shell gelatin capsules, compressed into tablets, or incorporated directly with the food of the diet. For oral therapeutic administration, the compounds may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non toxic in the amounts employed.

Some compositions or dosage forms may be a liquid, or may comprise a solid phase dispersed in a liquid.

Zoledronic acid may be formulated for parental or intraperitoneal administration. Solutions of the active compounds as free acids or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

In some embodiments, an oral dosage form may comprise a silicified microcrystalline cellulose such as Prosolv. For example, about 20% (wt/wt) to about 70% (wt/wt), about 10% (wt/wt) to about 20% (wt/wt), about 20% (wt/wt) to about 40% (wt/wt), about 25% (wt/wt) to about 30% (wt/wt), about 40% (wt/wt) to about 50% (wt/wt), or about 45% (wt/wt) to about 50% (wt/wt) silicified microcrystalline cellulose may be present in an oral dosage form or a unit of an oral dosage form.

In some embodiments, an oral dosage form may comprise a crosslinked polyvinylpyrrolidone such as crospovidone. For example, about 1% (wt/wt) to about 10% (wt/wt), about 1% (wt/wt) to about 5% (wt/wt), or about 1% (wt/wt) to about 3% (wt/wt) crosslinked polyvinylpyrrolidone may be present in an oral dosage form or a unit of an oral dosage form.

In some embodiments, an oral dosage form may comprise a fumed silica such as Aerosil. For example, about 0.1% (wt/wt) to about 10% (wt/wt), about 0.1% (wt/wt) to about 1% (wt/wt), or about 0.4% (wt/wt) to about 0.6% (wt/wt) fumed silica may be present in an oral dosage form or a unit of an oral dosage form.

In some embodiments, an oral dosage form may comprise magnesium stearate. For example, about 0.1% (wt/wt) to about 10% (wt/wt), about 0.1% (wt/wt) to about 1% (wt/wt), or about 0.4% (wt/wt) to about 0.6% (wt/wt) magnesium stearate may be present in an oral dosage form or a unit of an oral dosage form.

An oral dosage form comprising zoledronic acid or another bisphosphonate may be included in a pharmaceutical product comprising more than one unit of the or dosage form.

A pharmaceutical product containing or dosage forms for daily use can contain 28, 29, 30, or 31 units of the oral dosage form for a monthly supply. An approximately 6 week daily supply can contain 40 to 45 units of the oral dosage form. An approximately 3 month daily supply can contain 85 to 95 units of the oral dosage form. An approximately six-month daily supply can contain 170 to 200 units of the oral dosage form. An approximately one year daily supply can contain 350 to 380 units of the oral dosage form.

A pharmaceutical product containing oral dosage forms for weekly use can contain 4 or 5 units of the oral dosage form for a monthly supply. An approximately 2 month weekly supply can contain 8 or 9 units of the oral dosage form. An approximately 6 week weekly supply can contain about 6 units of the oral dosage form. An approximately 3 month weekly supply can contain 12, 13 or 14 units of the oral dosage form. An approximately six-month weekly supply can contain 22 to 30 units of the oral dosage form. An approximately one year weekly supply can contain 45 to 60 units of the oral dosage form.

A pharmaceutical product may accommodate other dosing regimes. For example, a pharmaceutical product may comprise 5 to 10 units of the oral dosage form, wherein each unit of the oral dosage form contains about 40 mg to about 150 mg of zoledronic acid. Some pharmaceutical products may comprise 1 to 10 units of the oral dosage form, wherein the product contains about 200 mg to about 2000 mg of zoledronic acid. For such a product, each unit of the oral dosage form may be taken daily for 1 to 10 days or 5 to 10 days during a month, such as at the beginning of a month.

Some oral dosage forms comprising zoledronic acid or a salt thereof may have enteric coatings or film coatings.

A subject composition may be prepared by adding Compound 1 and/or Compound 2 to zoledronic acid in the desired amount. While there may be many ways to prepare Compound 1 and Compound 2, a useful method of preparing these compounds is provided in Example 1 below. Additionally, in some methods of preparing the disodium salt or the diacid form of zoledronic acid, Compound 1 and/or Compound 2 may be formed as side products. If appropriate, some part of Compound 1 and/or Compound 2 naturally present in a zoledronic acid product may be removed to obtain a desired amount of Compound 1 and/or Compound 2.

There are a number of ways that some part of Compound 1 and/or Compound 2 may be removed from a zoledronic acid product. For example, HPLC, preparative TLC, crystallization, sublimation, or zone purification may be employed. Solvents that may be useful in HPLC, TLC, or crystallization, may include, but are not limited to, water or organic solvents, such as hexanes, diethyl ether, ethyl acetate, methyl acetate, acetone, acetic acid, acetonitrile, tetrahydrofuran, ethanol, methanol, isopropyl alcohol, chloroform, diethyl ether, toluene, dimethylformamide, benzene, etc. Gradients, or two solvent systems may be employed as well. For example, an HPLC separation may begin by elution with water, after some time eluting with water, an organic solvent, such as acetonitrile, methanol, ethanol, ethyl acetate, acetone, acetic acid, methyl acetate, or an other solvent could gradually be added to the water, or may replace the water entirely. Similarly, crystallization or recrystallization may employ a single solvent, or a combination of solvents. For example, zoledronic acid or a salt thereof, such as a disodium salt, might be recrystallized from water, ethanol, methanol, diethyl ether, methyl acetate, acetic acid, etc., or a combination of these solvents or others. In some embodiments, zoledronic acid or a salt thereof, such as a disodium salt, may be dissolved in one solvent, such as water or acetic acid, and crystallized by a second solvent or solvent system, such as hexane, diethyl ether, chloroform, dichloromethane, ethyl acetate, methyl acetate, acetic acid, ethanol, methanol, or a combination thereof. In some embodiments, a disodium salt of zoledronic acid is dissolved in water, and then crystallized by adding hexane. In some embodiments, a disodium salt of zoledronic acid is dissolved in water, and then crystallized by adding diethyl ether. In some embodiments, a disodium salt of zoledronic acid is dissolved in water, and then crystallized by adding chloroform. In some embodiments, a disodium salt of zoledronic acid is dissolved in water, and then crystallized by adding dichloromethane. In some embodiments, a disodium salt of zoledronic acid is dissolved in water, and then crystallized by adding ethyl acetate. In some embodiments, a disodium salt of zoledronic acid is dissolved in water, and then crystallized by adding methyl acetate. In some embodiments, a disodium salt of zoledronic acid is dissolved in water, and then crystallized by adding acetic acid. In some embodiments, a disodium salt of zoledronic acid is dissolved in water, and then crystallized by adding ethanol. In some embodiments, a disodium salt of zoledronic acid is dissolved in water, and then crystallized by adding methanol. For embodiments employing water and a second solvent, the ratio of water to the second solvent (water:second solvent) may be about 1:100 to about 100:1, about 1:10 to about 1:5, about 1:5 to about 1:4, about 1:4 to about 1:3, about 1:3 to about 1:2, about 1:2 to about 1:1, about 1:1 to about 2:1, about 2:1 to about 3:1, about 3:1 to about 4:1, about 4:1 to about 5:1, or about 1:1 to about 10:1.

In some embodiments, a combination of two methods recited in the paragraph above may be employed, such as HPLC or TLC and crystallization. In some embodiments, a method may be repeated, such as HPLC, preparative TLC, crystallization, sublimation, or zone purification. In some embodiments, a purification method recited in the paragraph above may be performed twice. In some embodiments, a purification method recited in the paragraph above may be performed three or four times.

Example 1

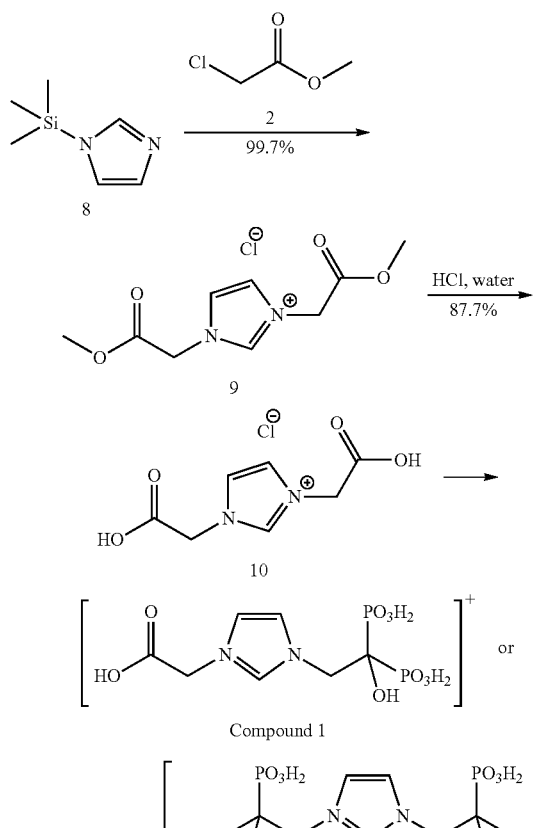

1,3-Bis(2-methoxy-2-oxoethyl)-1H-imidazol-3-ium chloride (9)

Methyl chloroacetate (2; 29.8 mL, 338.6 mmol, 2.0 eq) was added drop-wise to 1-(trimethylsilyl)-1H-imidazole (8; 25.0 mL, 169.3 mmol). The mixture was heated at 60° C. for 24 hours. The mixture was cooled to room temperature, washed with $Et_2O$ (3×500 mL) and dried in vacuo yielding 9 (41.97 g, 168.8 mmol, 99.7%) as a white solid.

1,3-Bis(carboxymethyl)1H-imidazol-3-ium chloride (10)

To 1,3-bis(2-methoxy-2-oxoethyl)-1H-imidazol-3-ium chloride (9; 41.00 g, 164.88 mmol, 1 eq.) was added 37% aq. HCl (30.03 mL, 362.74 mmol, 2.2 eq.). The mixture was stirred under reflux for 0.5 hour. The mixture was concentrated and the remaining solid was washed with acetone (2×200 mL) and $Et_2O$ (3×200 mL). Drying in in vacuo gave 10 (31.89 g, 144.55 mmol, 87.7%) as a white solid.

Compound 1:

Compound 10 is reacted with an equimolar amount of phosphorous acid, followed by an equimolar amount of phosphorous trichloride, and an excess of water to form Compound 1, which is precipitated from ethanol.

Compound 2:

1,3-Bis(carboxymethyl)-1H-imidazol-3-ium chloride (10, 2.00 g, 9 mmol, 1.0 eq) and $H_3PO_3$ (7.37 g, 90 mmol, 10 eq) were dissolved in toluene (10 mL) and heated to 70° C. The reaction mixture was stirred at this temperature for 20 min before $PCl_3$ (16 mL, 180 mmol, 20 eq) was added within 30 min. The reaction mixture was then heated to 95° C. and stirred at this temperature for 2 h. Then, aq. HCl (30 mL, 37% HCl and 5 mL $H_2O$) was added. The reaction mixture was heated to 100° C. and stirred at this temperature for 7 h, for 2 d stirred at room temperature and then filtered. The filtrate was cooled in an ice bath and added within 45 min to absolute EtOH (90 mL). The resulting turbid solution was stirred for 1 h at room temperature before the solid was filtered off. The filter cake (46-1) was isolated and analyzed by 2D-NMR spectroscopy and mass spectrometry (m/z=477). The filtrate was concentrated in vacuo to give residue 46-2. Five hundred mg of this residue were treated with aq. NaOH (150 mg in 3.5 mL $H_2O$) and to this was added EtOH (7 mL). After standing overnight the liquid was decanted and the resulting solid (46-M4) was analyzed NMR and mass spectrometry (m/z=477).

The following embodiments are contemplated:

Embodiment 1

A pharmaceutical composition comprising:

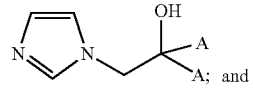
(Compound A)

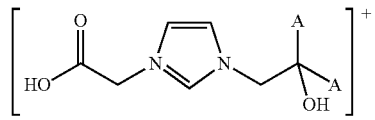
(Compound B)

in an amount that is less than 0.1% w/w, and greater than 0% w/w, based upon the total weight of Compound A, Compound B, and Compound C; or

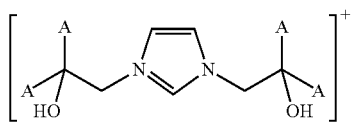
(Compound C)

in an amount that is less than 0.1% w/w, and greater than 0% w/w, based upon the total weight of Compound A, Compound B, and Compound C;

wherein each A is independently an acidic functional group.

Embodiment 2

A pharmaceutical composition comprising:

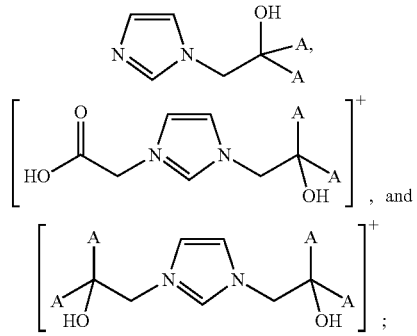

, and wherein each A is independently an acidic functional group.

Embodiment 3

The composition of embodiment 1 or 2, wherein each A is $CO_2H$.

Embodiment 4

The composition of embodiment 1 or 2, wherein each A is $SO_3H$.

Embodiment 5

The pharmaceutical composition of embodiment 1 or 2, wherein is present in an amount that is less than 0.05% w/w, and greater than 0% w/w, based upon the total weight of Compound A, Compound B, and Compound C.

Embodiment 6

The pharmaceutical composition of embodiment 1, 2, 3, 4, or 5, wherein is present in an amount that is less than 0.05% w/w, and greater than 0% w/w, based upon the total weight of Compound A, Compound B, and Compound C.

Embodiment 7

A pharmaceutical composition comprising: zoledronic acid; and (Compound 1)

in an amount that is less than 0.1% w/w, and greater than 0% w/w, based upon the total weight of zoledronic acid, Compound 1, and Compound 2; or (Compound 2)

in an amount that is less than 0.1% w/w, and greater than 0% w/w, based upon the total weight of zoledronic acid, Compound 1, and Compound 2.

Embodiment 8

A pharmaceutical composition comprising:

zoledronic acid,

, and

.

Embodiment 9

The pharmaceutical composition of embodiment 7 or 8, wherein is present in an amount that is less than 0.08% w/w, and greater than 0% w/w, based upon the total weight of zoledronic acid, Compound 1, and Compound 2.

Embodiment 10

The pharmaceutical composition of embodiment 7, 8, or 9, wherein

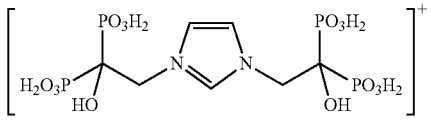

is present in an amount that is less than 0.08% w/w, and greater than 0% w/w, based upon the total weight of zoledronic acid, Compound 1, and Compound 2.

Embodiment 11

The pharmaceutical composition of embodiment 7, 8, 9, or 10, wherein

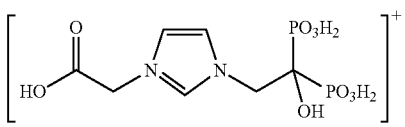

is present in an amount that is less than about 0.05%, and greater than 0% w/w, based upon the total weight of zoledronic acid, Compound 1, and Compound 2.

Embodiment 12

The pharmaceutical composition of embodiment 11, wherein

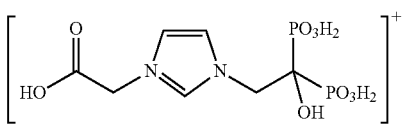

is present in an amount that is less than about 0.02%, and greater than 0% w/w, based upon the total weight of zoledronic acid, Compound 1, and Compound 2.

Embodiment 13

The pharmaceutical composition of embodiment 7, 8, 9, 10, 11, or 12, wherein

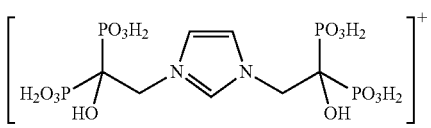

is present in an amount that is less than about 0.05% or about 0.02%, and greater than 0% w/w, based upon the total weight of zoledronic acid, Compound 1, and Compound 2.

Embodiment 14

The pharmaceutical composition of embodiment 1, 2, 3, 4, 5, 6, 7, 8, 9, 10, 11, 12, or 13, wherein the zoledronic acid is present in a salt form.

Embodiment 15

The pharmaceutical composition of embodiment 14, wherein the zoledronic acid is present in a sodium salt form.

Embodiment 16

The pharmaceutical composition of embodiment 15, wherein the zoledronic acid is present in a disodium salt form.

Embodiment 17

A dosage form comprising the pharmaceutical composition of embodiment 1, 2, 3, 4, 5, 6, 7, 8, 9, 10, 11, 12, 13, 14, 15, or 16.

Embodiment 18

The dosage form of embodiment 17, wherein the dosage form is an oral dosage form.

Embodiment 19

A method of treating a disease or condition related to bone, cancer, or pain, comprising administering a dosage form of embodiment 17 or 18 to a mammal in need thereof.

Embodiment 20

A method of relieving inflammatory pain comprising administering an oral dosage form of embodiment 18 to a mammal in need thereof, wherein the mammal receives a total monthly dose of zoledronic acid that is about 800 mg/m$^2$ or less based upon the body surface area of the mammal.

Embodiment 21

The method of embodiment 20, wherein the mammal is a human being that receives a total monthly dose of zoledronic acid that is about 30 mg/m$^2$ to about 700 mg/m$^2$.

Embodiment 22

The method of embodiment 20 or 21, wherein the total monthly dose is administered in 4 or 5 weekly doses.

Embodiment 23

The method of embodiment 20 or 21, wherein the total monthly dose is administered in 28 to 31 daily doses.

Embodiment 24

The method of embodiment 20 or 21, wherein the total monthly dose is administered in 5 to 10 individual doses during the month.

Embodiment 25

The method of embodiment 20 or 21, wherein the mammal is a human being that receives a total weekly dose of zoledronic acid that is about 10 mg to about 300 mg.

Embodiment 26

The method of embodiment 25 wherein the total weekly dose is a single dose, administered once a week.

Embodiment 27

The method of embodiment 25, wherein the total weekly dose is administered in 2 to 7 individual doses during the week.

Embodiment 28

The method of embodiment 20, wherein the mammal is a human being that receives a total weekly dose of zoledronic acid that is about 10 mg to about 150 mg.

Embodiment 29

The method of embodiment 20, 21, 22, 23, 24, 25, 26, 27, or 28, wherein the mammal experiences significant pain relief more than 3 hours after administration of the dosage form.

Embodiment 30

The method of embodiment 29, wherein the mammal experiences significant pain relief during at least a part of a time from about 3 hours to about 24 hours after administration of the dosage form.

Embodiment 31

The method of embodiment 29, wherein the mammal experiences significant pain relief during at least a part of a time from about 3 hours to about 3 weeks after administration of the dosage form.

Embodiment 32

A method of relieving inflammatory pain comprising administering an oral dosage form of embodiment 18 to a mammal in need thereof, wherein the oral dosage form contains about 10 mg/m$^2$ to about 20 mg/m$^2$ of zoledronic acid based upon the body surface area of the mammal.

Embodiment 33

The method of embodiment 32, wherein the oral dosage form contains about 15 mg/m$^2$ to about 20 mg/m$^2$ of zoledronic acid based upon the body surface area of the mammal.

Embodiment 34

A method of relieving inflammatory pain comprising orally administering, by one or more dosage forms of embodiment 18, to a mammal in need thereof, about 300 mg/m$^2$ to about 600 mg/m$^2$ of zoledronic acid per month to the mammal, based upon the body surface area of the mammal.

Embodiment 35

The method of embodiment 34, comprising orally administering about 450 mg/m$^2$ to about 600 mg/m$^2$ of zoledronic acid per month to the mammal, based upon the body surface area of the mammal.

Embodiment 36

The method of embodiment 20, 21, 22, 23, 24, 25, 26, 27, 28, 29, 30, 31, 32, 33, 34, or 35, wherein the mammal is not suffering from bone metastasis.

Embodiment 37

The method of embodiment 20, 21, 22, 23, 24, 25, 26, 27, 28, 29, 30, 31, 32, 33, 34, or 35, wherein the mammal is not suffering from cancer.

Embodiment 38

The method of embodiment 19, 20, 21, 22, 23, 24, 25, 26, 27, 28, 29, 30, 31, 32, 33, 34, 35, 36, or 37, wherein the zoledronic acid is administered as a salt of a dianion of zoledronic acid.

Embodiment 39

A method of relieving pain associated with an arthritis comprising administering an oral dosage form of embodiment 18 to a human being in need thereof.

Embodiment 40

The method of embodiment 39, wherein the human being receives a total monthly dose of zoledronic acid that is about 40 mg to about 2000 mg.

Embodiment 41

The method of embodiment 40, wherein the total monthly dose is administered in 4 or 5 weekly doses.

Embodiment 42

The method of embodiment 40, wherein the total monthly dose is administered in 28 to 31 daily doses.

Embodiment 43

The method of embodiment 40, wherein the total monthly dose is administered in 5 to 10 individual doses during the month.

Embodiment 44

The method of embodiment 39 or 40, wherein the human being receives a total weekly dose of zoledronic acid that is about 100 mg to about 300 mg.

Embodiment 45

The method of embodiment 44, wherein the total weekly dose is a single dose, administered once a week.

Embodiment 46

The method of embodiment 44, wherein the total weekly dose is administered in 2 to 7 individual doses during the week.

Embodiment 47

The method of embodiment 44, 45, or 46, wherein the human being receives a total weekly dose of zoledronic acid that is about 10 mg to about 100 mg.

Embodiment 48

The method of any of embodiment 19, 20, 21, 22, 23, 24, 25, 26, 27, 28, 29, 30, 31, 32, 33, 34, 35, 36, 37, 38, 39, 40, 41, 42, 43, 44, 45, 46, or 47, wherein the human being experiences significant pain relief more than 3 hours after administration of the dosage form.

Embodiment 49

The method of embodiment 48, wherein the human being experiences significant pain relief during at least a part of a time from about 3 hours to about 24 hours after administration of the dosage form.

Embodiment 50

The method of embodiment 48, wherein the human being experiences significant pain relief during at least a part of a time from about 3 hours to about 3 weeks after administration of the dosage form.

Embodiment 51

The method or dosage form of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, wherein the dosage form contains about 10 mg/m² to about 20 mg/m² of zoledronic acid based upon the body surface area of the human being.

Embodiment 52

The method of embodiment 51, wherein the dosage form contains about 15 mg/m² to about 20 mg/m² of zoledronic acid based upon the body surface area of the human being.

Embodiment 53

The method of embodiment 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein about 50 mg/m² to about 200 mg/m² of zoledronic acid is orally administered per month, based upon the body surface area of the human being.

Embodiment 54

The method of embodiment 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein the dosage form contains about 80 mg/m² to about 150 mg/m² of zoledronic acid based upon the body surface area of the human being.

Embodiment 55

The method of embodiment 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein about 300 mg/m² to about 1000 mg/m² of zoledronic acid is orally administered per month, based upon the body surface area of the human being.

Embodiment 56

A method of preparing a dosage form for use in the treatment of a condition or disease related to bone, cancer, or pain, comprising determining an amount of a secondary compound in a composition comprising zoledronic acid or a salt thereof;
wherein the secondary compound is:

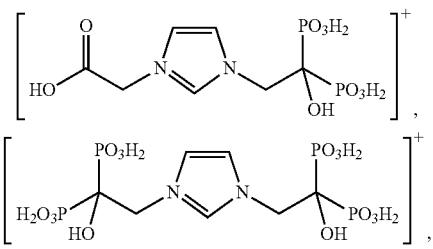

or a salt thereof.

Embodiment 57

A method of preparing a dosage form for use in the treatment of a condition or disease related to bone, cancer, or pain, comprising removing a secondary compound a composition comprising zoledronic acid or a salt thereof;
wherein an amount of the secondary compound is determined before removing the secondary compound from the composition comprising zoledronic acid or a salt thereof;
wherein the secondary compound is:

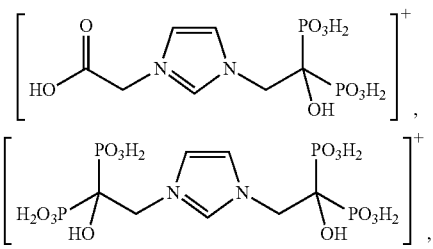

or a salt thereof.

Embodiment 58

The method of embodiment 55 or 56, wherein the amount of the secondary compound is determined to be greater than 0.1%.

Embodiment 59

The method of embodiment 55 or 56, wherein the amount of the secondary compound is determined to be greater than 0.08%.

Embodiment 60

A dosage form for use in the treatment of a condition or disease related to bone, cancer, or pain, wherein the dosage form is prepared by the method of embodiment 55, 56, 57, 58, or 59.

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:
1. A method of treating musculoskeletal pain comprising orally administering a pharmaceutical composition to a mammal in need thereof, wherein the pharmaceutical composition comprises:

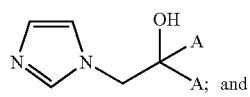

(Compound A)

and

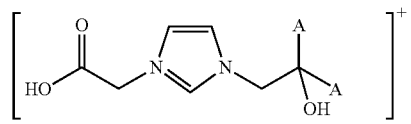

(Compound B)

in an amount that is less than 0.1% w/w, and greater than 0%; or

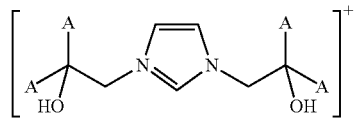

(Compound C)

in an amount that is less than 0.1% w/w, and greater than 0% w/w;
wherein any amount in % w/w is based upon the total weight of Compound A, Compound B, and Compound C;
wherein each A is independently an acidic functional group.

2. The method of claim 1, wherein the musculoskeletal pain comprises back pain, pain in extremity, joint pain, or muscle pain.

3. A method of treating joint pain not associated with cancer comprising orally administering a pharmaceutical composition to a human being suffering from joint pain not associated with cancer, wherein the pharmaceutical composition comprises:
   a) zoledronic acid; or
   b) one of the following:
      1) zoledronic acid and

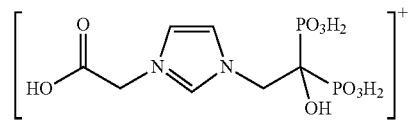

(Compound 1)

in an amount that is less than 0.1% w/w and greater than 0% w/w;
      2) zoledronic acid and

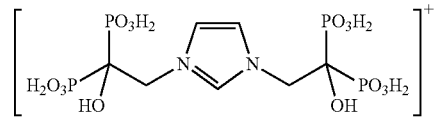

(Compond 2)

in an amount that is less than 0.1% w/w and greater than 0% w/w; or
      3) zoledronic acid and a combination of Compound 1 in an amount that is less than 0.1% w/w and greater than 0% w/w, and Compound 2 in an amount that is less than 0.1% w/w and greater than 0% w/w;
wherein the pharmaceutical composition is free of therapeutically active agents that are not zoledronic acid, Compound 1, and Compound 2;

wherein any amount in % w/w is based upon the total weight of zoledronic acid, Compound 1, and Compound 2; and wherein the bioavailability of zoledronic acid in the dosage form is about 1.1% to about 4%.

4. The method of claim 3, wherein the pharmaceutical composition is administered in an amount and frequency that results in an AUC of zoledronic acid, over a four week period, that is about 100 ng·h/mL to about 2000 ng·h/mL.

5. The method of claim 3, wherein the pharmaceutical composition is administered in an amount that results in an AUC of zoledronic acid, over a twenty-four hour period, that is about 20 ng·h/mL to about 500 ng·h/mL.

6. The method of claim 3, wherein the joint pain is located in the back.

7. The method of claim 6, wherein the pharmaceutical composition is administered in an amount such that a monthly dose of zoledronic acid is about 1 mg to about 600 mg.

8. The method of claim 3, wherein the joint pain comprises pain in an extremity.

9. The method of claim 8, wherein the pharmaceutical composition is administered in an amount such that a monthly dose of zoledronic acid is about 1 mg to about 600 mg.

10. The method of claim 3, wherein the pharmaceutical composition is administered in an amount such that a monthly dose of zoledronic acid is about 1 mg to about 600 mg.

11. A method of treating complex regional pain syndrome comprising orally administering a pharmaceutical composition to a human being suffering from complex regional pain syndrome, wherein the pharmaceutical composition comprises:
 a) zoledronic acid; or
 b) one of the following:
  1) zoledronic acid and (Compound 1)

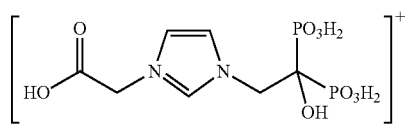

in an amount that is less than 0.1% w/w and greater than 0% w/w;
  2) zoledronic acid and (Compound 2)

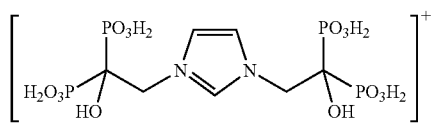

in an amount that is less than 0.1% w/w and greater than 0% w/w; or
  3) zoledronic acid and a combination of Compound 1 in an amount that is less than 0.1% w/w and greater than 0% w/w, and Compound 2 in an amount that is less than 0.1% w/w and greater than 0% w/w;
 wherein the pharmaceutical composition is free of therapeutically active agents that are not zoledronic acid, Compound 1, and Compound 2;

wherein any amount in % w/w is based upon the total weight of zoledronic acid, Compound 1, and Compound 2; and wherein the bioavailability of zoledronic acid in the dosage form is about 1.1% to about 4%.

12. The method of claim 11, wherein the pharmaceutical composition is administered in an amount such that a monthly dose of zoledronic acid is about 1 mg to about 600 mg.

13. The method of claim 11, wherein the pharmaceutical composition is administered in an amount and frequency that results in an AUC of zoledronic acid, over a four week period, that is about 100 ng·h/mL to about 2000 ng·h/mL.

14. The method of claim 11, wherein the pharmaceutical composition is administered in an amount that results in an AUC of zoledronic acid, over a twenty-four hour period, that is about 20 ng·h/mL to about 500 ng·h/mL.

15. A method of treating ankylosing spondylitis comprising orally administering a pharmaceutical composition to a human being suffering from ankylosing spondylitis, wherein the pharmaceutical composition comprises:
 a) zoledronic acid; or
 b) one of the following:
  1) zoledronic acid and (Compound 1)

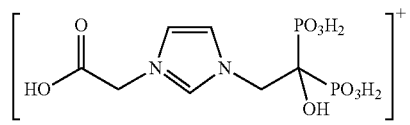

in an amount that is less than 0.1% w/w and greater than 0% w/w;
  2) zoledronic acid and (Compound 2)

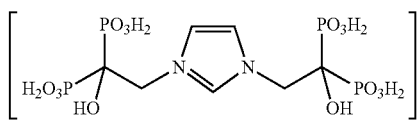

in an amount that is less than 0.1% w/w and greater than 0% w/w; or
  3) zoledronic acid and a combination of Compound 1 in an amount that is less than 0.1% w/w and greater than 0% w/w, and Compound 2 in an amount that is less than 0.1% w/w and greater than 0% w/w;
 wherein the pharmaceutical composition is free of therapeutically active agents that are not zoledronic acid, Compound 1, and Compound 2;

wherein any amount in % w/w is based upon the total weight of zoledronic acid, Compound 1, and Compound 2; and wherein the bioavailability of zoledronic acid in the dosage form is about 1.1% to about 4%.

16. The method of claim 15, wherein the pharmaceutical composition is administered in an amount such that a monthly dose of zoledronic acid is about 1 mg to about 600 mg.

17. The method of claim 15, wherein the pharmaceutical composition is administered in an amount and frequency that results in an AUC of zoledronic acid, over a four week period, that is about 100 ng·h/mL to about 2000 ng·h/mL.

18. The method of claim 15, wherein the pharmaceutical composition is administered in an amount that results in an AUC of zoledronic acid, over a twenty-four hour period, that is about 20 ng·h/mL to about 500 ng·h/mL.

19. The method of claim 3, wherein the bioavailability of zoledronic acid in the dosage form is from about 1.1% to about 3%.

20. The method of claim 11, wherein the bioavailability of zoledronic acid in the dosage form is from about 1.1% to about 3%.

21. The method of claim 15, wherein the bioavailability of zoledronic acid in the dosage form is from about 1.1% to about 3%.

\* \* \* \* \*